(12) United States Patent  (10) Patent No.: US 9,381,687 B2
Felts et al.  (45) Date of Patent: Jul. 5, 2016

(54) SYRINGE WITH INTEGRATED NEEDLE

(75) Inventors: John T. Felts, Alameda, CA (US); Jean-Pierre Giraud, Auburn, AL (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 709 days.

(21) Appl. No.: 13/805,835

(22) PCT Filed: Jun. 29, 2011

(86) PCT No.: PCT/US2011/042387
§ 371 (c)(1),
(2), (4) Date: Apr. 10, 2013

(87) PCT Pub. No.: WO2012/003221
PCT Pub. Date: Jan. 5, 2012

(65) Prior Publication Data
US 2013/0200549 A1  Aug. 8, 2013

Related U.S. Application Data

(60) Provisional application No. 61/359,434, filed on Jun. 29, 2010.

(51) Int. Cl.
*B29C 45/00* (2006.01)
*B29C 45/14* (2006.01)
(Continued)

(52) U.S. Cl.
CPC ........ *B29C 45/14065* (2013.01); *A61M 5/3129* (2013.01); *A61M 5/3202* (2013.01);
(Continued)

(58) Field of Classification Search
USPC ....................................................... 264/275
See application file for complete search history.

(56) References Cited

U.S. PATENT DOCUMENTS 3,118,448 A  1/1964  Gottschalk
5,494,712 A  2/1996  Hu et al.
(Continued)

FOREIGN PATENT DOCUMENTS

CN  201161026 Y  12/2008
CN  201350267 Y  11/2009
(Continued)

OTHER PUBLICATIONS

State Intellectual Property Office of the People's Republic of China, Notification of the First Office Action, in Application No. 201180032145.4, dated Jan. 30, 2014. (16 pages).
(Continued)

*Primary Examiner* — Jacob Thomas Minskey
(74) *Attorney, Agent, or Firm* — McAndrews, Held & Malloy, Ltd.

(57) ABSTRACT

A syringe (20) is disclosed including a needle (22) and a barrel (24). The needle can have an outside surface (32), a delivery outlet (34) at one end, a base (36) at the other end, and an internal passage (38) extending from the base to the delivery outlet. The barrel can have a generally cylindrical interior surface portion (40) defining a lumen. The barrel also can have a front passage (44) molded around and in fluid-sealing contact with the outside surface of the needle. A method of making such a syringe is also disclosed. A mold (80) for making the barrel defines a front opening of the barrel to be molded around and in fluid-sealing contact with the outside surface of the needle. The needle is positioned within the mold cavity, with its base abutting the core. The barrel is molded against the needle to join the barrel and the needle.

14 Claims, 9 Drawing Sheets

(51) Int. Cl.
*A61M 5/31* (2006.01)
*A61M 5/32* (2006.01)
*A61M 5/34* (2006.01)
*C23C 16/04* (2006.01)
*C23C 16/40* (2006.01)
*B29C 45/16* (2006.01)
*B29L 31/00* (2006.01)

(52) U.S. Cl.
CPC ......... *A61M 5/343* (2013.01); *B29C 45/14598* (2013.01); *B29C 45/1671* (2013.01); *C23C 16/045* (2013.01); *C23C 16/401* (2013.01); *A61M 2005/3117* (2013.01); *A61M 2005/3118* (2013.01); *B29C 45/14311* (2013.01); *B29C 45/1657* (2013.01); *B29L 2031/7544* (2013.01)

(56) References Cited

U.S. PATENT DOCUMENTS

| | | | |
|---|---|---|---|
| 5,679,413 A | 10/1997 | Petrmichl et al. | |
| 2003/0148030 A1* | 8/2003 | Vernon, Jr. | A61M 5/31513 427/255.28 |
| 2004/0176732 A1* | 9/2004 | Frazier | A61M 37/0015 604/345 |
| 2005/0251096 A1* | 11/2005 | Armstrong | A61M 5/14546 604/218 |
| 2007/0187280 A1 | 8/2007 | Haines | |
| 2009/0131878 A1* | 5/2009 | Kawamura | A61M 5/31515 604/228 |
| 2010/0145284 A1 | 6/2010 | Togashi | |
| 2010/0298738 A1* | 11/2010 | Felts | B05D 1/62 600/576 |

FOREIGN PATENT DOCUMENTS

| | | |
|---|---|---|
| EP | 0 329 041 | 8/1989 |
| FR | 891 892 | 3/1944 |
| GB | 614 003 | 12/1948 |
| JP | 2002068229 A | 3/2002 |
| WO | 2006/012281 | 2/2006 |
| WO | 2009/091895 | 7/2009 |

OTHER PUBLICATIONS

PCT, International Preliminary Report on Patentability and Written Opinion of the International Searching Authority for International Patent Application No. PCT/US2011/042387, mailed Jan. 8, 2013. (6 pages).
International Search Report and Written Opinion for International Patent Application No. PCT/US2011/042387, mailed Sep. 14, 2011.
Shimojima et al., "Structure and properties of multilayered siloxane-organic hybrid films prepared using long-chain organotrialkoxysilanes containing C=C double bonds." Journal of Materials Chemistry, vol. 17, No. 7, Jan. 1, 2007. XP55005947.
Mallikarjunan et al., "The Effect of Interfacial Chemistry of Metal Ion Penetration into Polymeric Films." MRS Proceedings, vol. 734, Jan. 1, 2001. XP55005837.
West Pharmaceuticals Services, Inc. "Daikyo Crystal Insert Needle Syringe System." 2010.
Japanese Patent Office, Notice of Reason(s) for Refusal, in Application No. 2013-518657 dated Apr. 28, 2015 (6 pages).

* cited by examiner

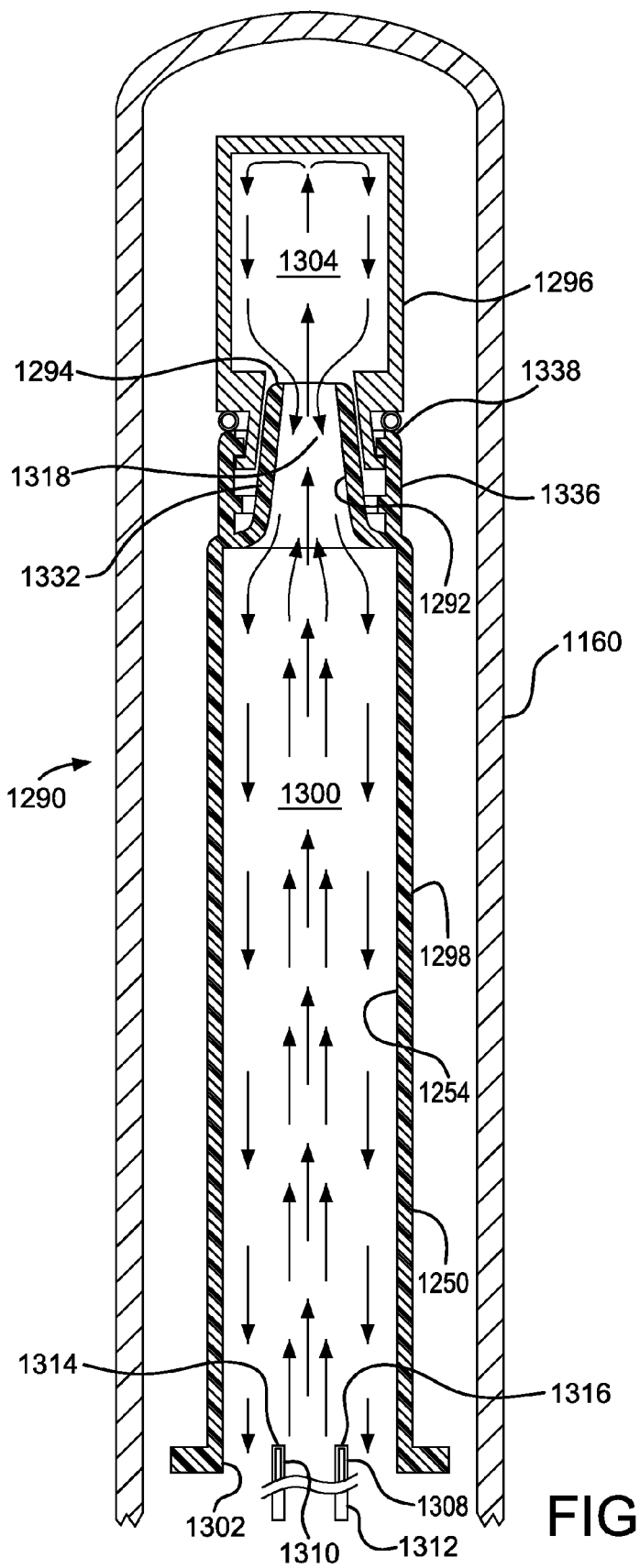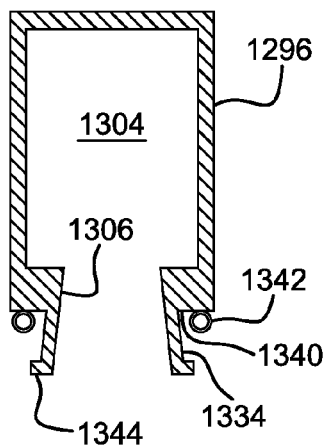
FIG. 9
FIG. 10

SYRINGE WITH INTEGRATED NEEDLE

BACKGROUND

The present disclosure relates generally to a syringe and to methods of making a syringe.

Two common types of syringes commonly sold are empty syringes and prefilled syringes. Empty syringes commonly are purchased by the end user and filled at the time of use. In some instances, the empty syringes are used more than once before disposing of them, though medical syringes in particular are normally used once. Prefilled syringes are filled in advance with a drug, saline solution, or other fluid to be dispensed and (particularly for medical use) placed within sterile packaging. Prefilled syringes thus are in contact with their contents for an extended period, in some cases for the entire shelf life of the prefilled syringe.

SUMMARY

An aspect of the invention is a syringe including a needle and a barrel. The needle of this aspect of the invention has an outside surface, a delivery outlet at one end, a base at the other end, and an internal passage extending from the base to the delivery outlet. The barrel has a, for example generally cylindrical, interior surface defining a lumen. The barrel also has a front passage molded around and in fluid-sealing contact with the outside surface of the needle.

The syringe of any embodiment optionally can further include a cap configured to isolate the delivery outlet of the needle from ambient air.

The cap of any embodiment optionally can further include a lumen having an opening defined by a rim and sized to receive the delivery outlet, and the rim can be seatable against an exterior portion of the barrel.

In the syringe of any embodiment, the barrel optionally can further include a generally hemispheric interior surface portion adjacent to its front passage.

In the syringe of any embodiment, the base of the needle optionally can be at least substantially flush with the hemispheric interior surface portion of the barrel.

The syringe of any embodiment optionally can further include a PECVD-applied barrier layer (also sometimes known as a barrier coating) on at least the hemispheric interior surface portion of the barrel.

In the syringe of any embodiment, the barrier layer (also sometimes known as a barrier coating) optionally can extend over at least a portion of the generally cylindrical interior surface portion of the barrel.

In the syringe of any embodiment, the barrier layer (also sometimes known as a barrier coating) optionally can form a barrier between the base of the needle and the generally cylindrical interior surface portion of the barrel.

In the syringe of any embodiment, the barrier layer (also sometimes known as a barrier coating) optionally can be made of SiOx, in which x optionally can be from about 1.5 to about 2.9.

In the syringe of any embodiment, the barrier layer (also sometimes known as a barrier coating) optionally can be from 1 to 100 nm thick.

In the syringe of any embodiment, the barrier layer (also sometimes known as a barrier coating) optionally can be effective to provide an oxygen barrier.

In the syringe of any embodiment, the syringe optionally can be prefilled with a fluid and the barrier layer (also sometimes known as a barrier coating) optionally can be effective to reduce leaching of the material of the barrel into the fluid.

The syringe of any embodiment optionally can further include a PECVD-applied lubricity coating on at least a portion of the generally cylindrical interior surface portion of the barrel.

In the syringe of any embodiment, the needle outside surface optionally can have a non-cylindrical portion within at least a portion of the barrel front passage for anchoring it within the barrel.

In the syringe of any embodiment, the needle optionally can be a hypodermic needle.

In the syringe of any embodiment, the delivery outlet of the needle optionally can be pointed.

The syringe of any embodiment optionally can further include a plunger sized and positioned to at least substantially seal against and move along the generally cylindrical interior surface portion of the barrel for expelling fluid from the delivery outlet of the needle.

The syringe of any embodiment optionally can further include a cap for covering the delivery outlet of the needle, the cap having a base and a coupling configured for securing the cap in a seated position on the barrel.

In the syringe of any embodiment, the delivery outlet of the needle optionally can be seated on the cap when the cap is secured on the barrel.

The syringe of any embodiment optionally can further include a flexible lip seal at the base of the cap for seating against the barrel when the cap is secured on the barrel.

The syringe of any embodiment optionally can further include a detent on one of the barrel and the cap and a projection on the other of the barrel and the cap, the projection being adapted to engage the detent when the cap is in its seated position on the barrel.

In the syringe of any embodiment, the barrel optionally can be injection molded.

In the syringe of any embodiment, the barrel optionally can be made in whole or in part of thermoplastic material.

In the syringe of any embodiment, the barrel optionally can be made in whole or in part of a cyclic olefin polymer (COP).

In the syringe of any embodiment, the barrel optionally can be made in whole or in part of a cyclic olefin copolymer (COC).

In the syringe of any embodiment, the barrel optionally can be made in whole or in part of a polyolefin.

In the syringe of any embodiment, the barrel optionally can be made in whole or in part of polypropylene.

In the syringe of any embodiment, the barrel optionally can be made in whole or in part of polyethylene.

In the syringe of any embodiment, the syringe barrel can be a double-walled vessel, for example having an inner wall made of PET and an outer wall made of COC.

Another aspect of the invention is a method of making a syringe. In the method of this aspect of the invention, a needle is provided having an outside surface, a delivery outlet at one end, a base at the other end, and an internal passage extending from the base to the delivery outlet. A mold is provided for making a barrel having a, for example, generally cylindrical interior surface defining a lumen. The mold defines a front opening of the barrel to be molded around and in fluid-sealing contact with the outside surface of the needle. The mold includes a core and a cavity. At least a portion of the needle is positioned within the mold cavity, with its base abutting the core or even extending into the core and at least a portion of its outside surface exposed within the cavity. Moldable material is injected into the mold cavity, forming the barrel against the portion of the needle outside surface exposed within the cavity to join the barrel and the needle.

The method of any embodiment optionally can further include:
   providing a strand having first and second ends; and
   before injecting moldable material into the mold cavity, threading the strand into at least a portion of the internal passage of the needle.

In the method of any embodiment, the first end of the strand optionally can be secured to the mold core.

In the method of any embodiment, the second end of the strand optionally can be secured to the mold cavity.

The method of any embodiment optionally can further include, before injecting moldable material into the mold cavity, providing at least one side draw abutting a portion of the outside surface of the needle which will be exposed in the finished syringe, the side draw being configured and positioned to keep the barrel material away from the abutted portion of the outside surface of the needle.

In the method of any embodiment, at least one side draw optionally can position the needle in the mold.

The method of any embodiment optionally can further include over-molding a cap on the syringe, the cap being configured to isolate the delivery outlet of the needle from ambient air.

In the method of any embodiment, the cap optionally can be over-molded into contact with at least the delivery outlet of the needle.

In the method of any embodiment, the cap optionally can be over-molded from a thermoplastic elastomer.

In the method of any embodiment, the cap optionally can have an internal portion 96 and an external portion, and the method can further include:
   molding the cap internal portion out of contact with the syringe barrel;
   assembling the cap internal portion and the syringe barrel; and
   over-molding additional resin defining the external portion of the cap over the internal portion of the cap.

In the method of any embodiment, the external and internal portions 98 and 96 of the cap 26 optionally can be integrally joined by the over-molding.

In the method of any embodiment, injecting moldable material into the mold cavity, forming the barrel, optionally can be the first shot and over-molding a cap on the syringe optionally can be the second shot of a two-shot molding process.

The method of any embodiment optionally can further include, after joining the barrel and the needle, forming a plasma within the lumen of the barrel, introducing an organosilicon gas within the lumen of the barrel, and depositing a coating of a nongas organosilicon material on at least one of the generally cylindrical interior surface portion and the generally hemispherical interior surface portion of the barrel.

The method of any embodiment optionally can further include depositing the coating of a nongas organosilicon material between the base of the needle and the barrel.

In the method of any embodiment, the organosilicon material coating optionally can be SiOx, in which x optionally can be from about 1.5 to about 2.9.

In the method of any embodiment, the organosilicon material optionally can be a lubricity coating.

In the method of any embodiment, the lubricity coating can be provided on at least a portion of the interior surface portion of the barrel.

In the method of any embodiment, the needle optionally can be made of electrically conductive material.

In the method of any embodiment, the base of the needle optionally can be positioned within the mold cavity at least substantially flush with the mold core.

In the method of any embodiment, the moldable material optionally can be thermoplastic material.

In the method of any embodiment, the moldable material optionally can include a cyclic olefin polymer (COP).

In the method of any embodiment, the moldable material optionally can include a cyclic olefin copolymer (COC).

In the method of any embodiment, the moldable material optionally can include a polyolefin.

In the method of any embodiment, the moldable material optionally can include polypropylene.

In the method of any embodiment, the moldable material optionally can include polyethylene.

In the method of any embodiment, the moldable material optionally can include polynaphthalene.

BRIEF DESCRIPTION OF DRAWING FIGURES

FIG. 1 is a longitudinal section of a syringe with a staked needle as contemplated here.

FIGS. 2A, 2B, and 2C are progressive enlargements of a longitudinal section similar to FIG. 1 of another embodiment.

FIG. 9 is a diagrammatic view showing a temporary vessel for placement on a syringe during PECVD treatment. A different type of syringe is shown there; the syringe of FIG. 1 can be substituted.

FIG. 10 shows an isolated view of the temporary vessel.

The following reference characters are used in this specification. Like reference characters indicate like or corresponding parts.

Figure 1:
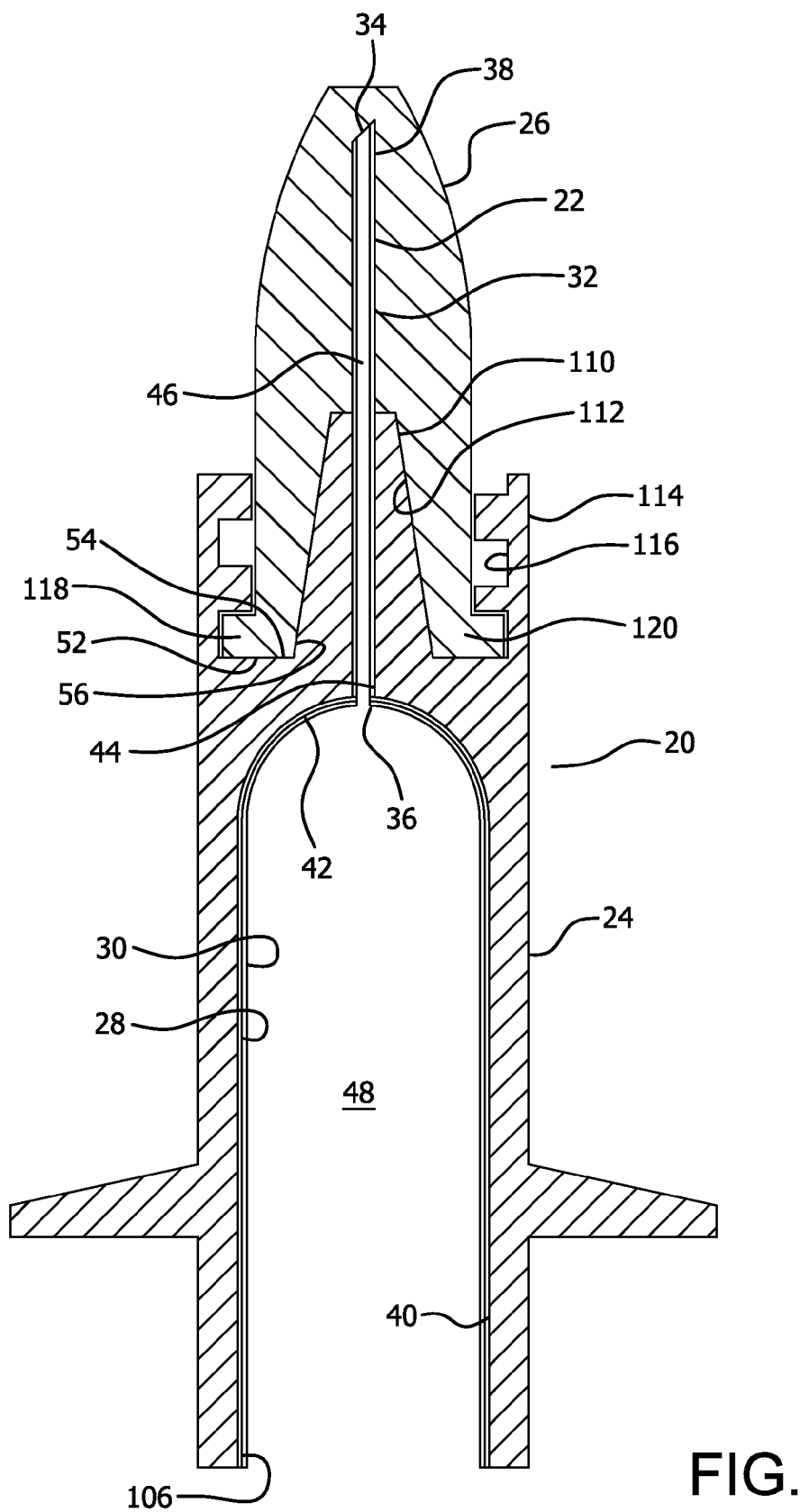

| | |
|---|---|
| 20 | Syringe |
| 22 | Needle |
| 24 | Barrel |
| 26 | Cap |
| 28 | Barrier layer |
| 30 | Lubricity coating |
| 32 | Outside surface |
| 34 | Delivery outlet |
| 36 | Base (of 22) |
| 38 | Internal passage |
| 40 | Generally cylindrical interior surface portion |
| 42 | Generally hemispheric interior surface portion |
| 44 | Front passage |
| 46 | Lumen |
| 48 | Lumen |
| 50 | Ambient air |
| 52 | Rim |
| 54 | Exterior portion (of 24) |

| | |
|---|---|
| 56 | Opening |
| 58 | Fluid |
| 60 | Material (of 24) |
| 64 | Non-cylindrical portion (of 22) |
| 66 | Plunger |
| 68 | Base |
| 70 | Coupling |
| 72 | Flexible lip seal |
| 74 | Detent |
| 76 | Projection |
| 80 | Mold |
| 82 | Mold cavity |
| 84 | Mold core |
| 86 | Strand |
| 88 | First end (of 86) |
| 90 | Second end (of 86) |
| 92 | Side draw |
| 94 | Side draw |
| 96 | Internal portion (of 26) |
| 98 | External portion (of 26) |
| 100 | Plasma |
| 102 | Organosilicon gas |
| 104 | Plunger tip |
| 106 | Back opening (of 24) |
| 108 | Luer fitting (of 24) |
| 110 | Tapered nose (of 20) |
| 112 | Tapered throat (of 26) |
| 114 | Collar (of 20) |
| 116 | Interior thread (of 114) |
| 118 | Dog (of 26) |
| 120 | Dog (of 26) |
| 122 | Syringe barrel (FIG. 2) |
| 124 | Cap (FIG. 2) |
| 126 | Cap (FIG. 3) |
| 128 | Attachment point |
| 130 | Barrel (FIG. 3) |
| 132 | Cap material |
| 134 | Undercut |
| 138 | Projections (of 126) |
| 140 | Finger grips |
| 142 | Pin |
| 180 | Vessel |
| 182 | Opening |
| 184 | Closed end |
| 186 | Wall |
| 188 | Interior surface |
| 190 | Barrier layer |
| 192 | Vessel port |
| 194 | Vacuum duct |
| 196 | Vacuum port |
| 198 | Vacuum source |
| 268 | Vessel |
| 408 | Inner wall |
| 410 | Outer wall |
| 1100 | O-ring (of 192) |
| 1102 | O-ring (of 196) |
| 1104 | Gas inlet port |
| 1108 | Probe (counter electrode) |
| 1110 | Gas delivery port (of 1108) |
| 1114 | Housing (of 1150) |
| 1116 | Collar |
| 1118 | Exterior surface |
| 1128 | Coating station |
| 1144 | PECVD gas source |
| 1150 | Vessel holder |
| 1160 | Electrode |
| 1162 | Power supply |
| 1164 | Sidewall (of 1160) |
| 1166 | Sidewall (of 1160) |
| 1168 | Closed end (of 1160) |
| 1250 | Syringe barrel |
| 1254 | Interior surface (of 1250) |
| 1290 | Apparatus for coating, for example, 1250 |
| 1292 | Inner surface (of 1294) |
| 1294 | Restricted opening (of 1250) |
| 1296 | Processing vessel |
| 1298 | Outer surface (of 1250) |
| 1300 | Lumen (of 1250) |
| 1302 | Larger opening (of 1250) |
| 1304 | Processing vessel lumen |
| 1306 | Processing vessel opening |
| 1308 | Inner electrode |
| 1310 | Interior passage (of 1308) |
| 1312 | Proximal end (of 1308) |
| 1314 | Distal end (of 1308) |
| 1316 | Distal opening (of 1308) |
| 1318 | Plasma |
| 1332 | First fitting (male Luer taper) |
| 1334 | Second fitting (female Luer taper) |
| 1336 | Locking collar (of 1332) |
| 1338 | First abutment (of 1332) |
| 1340 | Second abutment (of 1332) |
| 1342 | O-ring |
| 1344 | Dog |
| 1482 | Vessel holder body |
| 1484 | Upper portion (of 1482) |
| 1486 | Base portion (of 1482) |
| 1488 | Joint (between 1484 and 1486) |
| 1490 | O-ring |
| 1492 | Annular pocket |
| 1494 | Radially extending abutment surface |
| 1496 | Radially extending wall |
| 1498 | Screw |
| 1500 | Screw |
| 1502 | Vessel port |
| 1504 | Second O-ring |
| 1506 | Inner diameter |
| 1508 | Vacuum duct (of 1482) |

DETAILED DESCRIPTION

A syringe with an integrated needle is described. This construction has the optional advantages of reducing the number assembly steps, eliminating exposure of workers to unshielded needles during assembly and/or eliminating the need for adhesives to bond the needle to the syringe. Eliminating adhesives potentially is a benefit to reduce interaction between an injectable drug and the syringe (for pre-filled syringes).

Referring to FIG. 1, an embodiment of a syringe 20 is shown including a needle 22 and a barrel. Optionally, a cap 26 can be fabricated for use with the syringe 20.

The needle 22, which can be a hypodermic needle (mainly distinguished by being sharpened and otherwise suitable to pierce human or animal tissue) or an unsharpened needle or nozzle has an outside surface 32, a delivery outlet 34 at one end, a base 36 at the other end, and an internal passage 38 extending from the base 36 to the delivery outlet 34. Optionally, the delivery outlet 34 of the needle 22 can be sharpened or otherwise pointed. The needle 22 of any embodiment can be made of electrically conductive material. For example, the needle 22 can be made of drawn steel.

The barrel has a generally cylindrical interior surface portion 40 defining a lumen 48. The barrel has a front passage 44 molded around and in fluid-sealing contact with the outside surface 32 of the needle 22. The barrel of this embodiment also has a generally hemispheric interior surface portion 42 adjacent to its front passage 44. Optionally, the base 36 of the needle 22 can be at least substantially flush with the hemispheric interior surface portion 42 of the barrel. A needle 22 flush with the syringe interior surface 42, for example the hemispherical surface portion 42 of the syringe 20, can provide a smooth transition between the needle 22 and the syringe interior surface 42.

The barrel can be injection molded or otherwise formed. The barrel can be made of thermoplastic material. Several examples of suitable thermoplastic material are a polyolefin, for example a cyclic olefin polymer (COP), a cyclic olefin copolymer (COC), polypropylene, or polyethylene (for example, low-density polyethylene—LDPE—or high-density polyethylene—HDPE. The syringe barrel can also be made of polyethylene terephthalate (PET), polycarbonate resin, polynaphthalene (PEN), or any other suitable material. Optionally, a material can be selected that can withstand vacuum and maintain sterility within the syringe.

Figure 11:
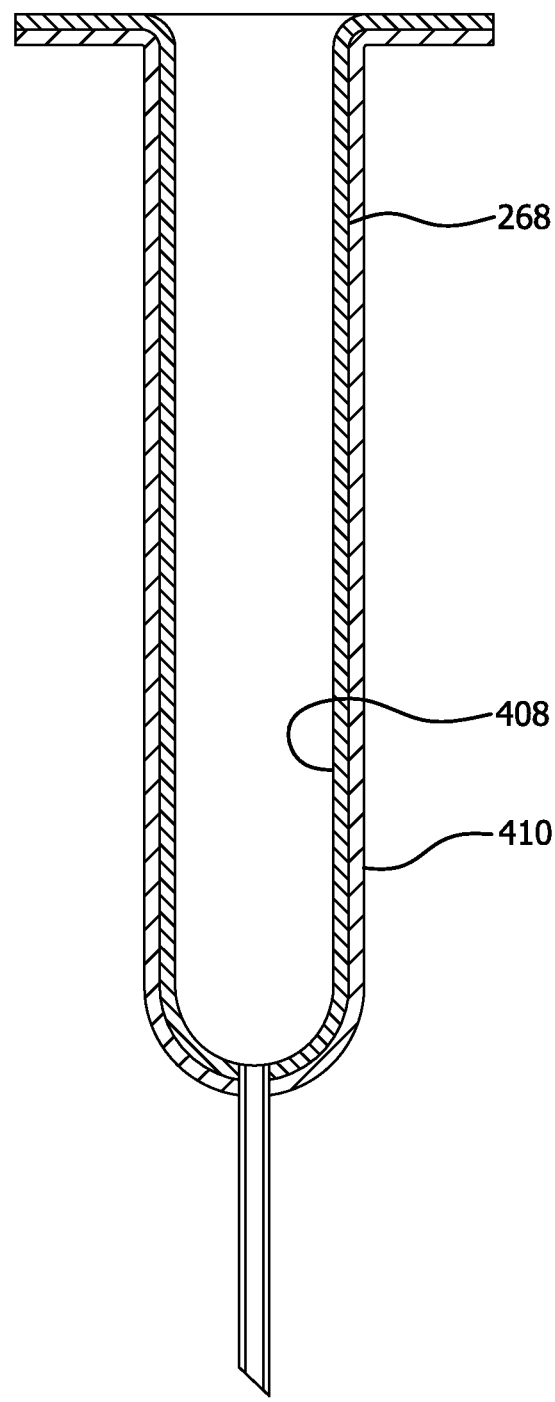
FIG. 11 shows a longitudinal section of a double-walled vessel.

In an embodiment, illustrated in FIG. 11, the syringe barrel 268 can be a double-walled vessel having an inner wall 408 and an outer wall 410, respectively made of the same or different materials. One particular embodiment of this type can be made with one wall molded from a cyclic olefin copolymer (COC) and the other wall molded from a polyester such as polyethylene terephthalate (PET), with an SiOx coating as previously described on the interior surface 412. As needed, a tie coating or layer can be inserted between the inner and outer walls to promote adhesion between them. An advantage of this wall construction is that walls having different properties can be combined to form a composite having the respective properties of each wall.

As one example, the inner wall 408 can be made of PET coated on the interior surface 412 with an SiOx barrier layer, and the outer wall 410 can be made of COC. PET coated with SiOx, as shown elsewhere in this specification, is an excellent oxygen barrier, while COO is an excellent barrier for water vapor, providing a low water vapor transition rate (WVTR). This composite vessel can have superior barrier properties for both oxygen and water vapor. This construction is contemplated, for example, for a prefilled syringe that contains an aqueous reagent as manufactured, and has a substantial shelf life, so it should have a barrier preventing transfer of water vapor outward or transfer of oxygen or other gases inward through its composite wall during its shelf life.

As another example, the inner wall 408 can be made of COO coated on the interior surface 412 with an SiOx barrier layer, and the outer wall 410 can be made of PET. This construction is contemplated, for example, for a prefilled syringe that contains an aqueous sterile fluid as manufactured. The SiOx barrier will prevent oxygen from entering the syringe through its wall. The COO inner wall will prevent ingress or egress of other materials such as water, thus preventing the water in the aqueous sterile fluid from leaching materials from the wall material into the syringe. The COO inner wall is also contemplated to prevent water derived from the aqueous sterile fluid from passing out of the syringe (thus undesirably concentrating the aqueous sterile fluid), and will prevent non-sterile water or other fluids outside the syringe from entering through the syringe wall and causing the contents to become non-sterile. The COO inner wall is also contemplated to be useful for decreasing the breaking force or friction of the plunger against the inner wall of a syringe.

As another example, the interior surface 412 can be coated with a coating having the sum formula $Si_wO_xC_yH_z$, wherein w is 1, x is 0.5 to 2.4, y is 0.6 to 3, and z is from 2 to 9. The coating can be a (i) a lubricity coating having a lower frictional resistance than the uncoated surface; and/or (ii) a hydrophobic coating being more hydrophobic than the uncoated surface.

A vessel having a wall having an interior polymer layer enclosed by an exterior polymer layer can be made, for example, by introducing COO and polyester resin layers into an injection mold through concentric injection nozzles.

The syringe barrel 268 shown in FIG. 11 having an interior polymer layer enclosed by an exterior polymer layer also can be made from the inside out, for one example, by injection molding the inner wall in a first mold cavity, then removing the core and molded inner wall from the first mold cavity to a second, larger mold cavity, then injection molding the outer wall against the inner wall in the second mold cavity. Optionally, a tie layer can be provided to the exterior surface of the molded inner wall before over-molding the outer wall onto the tie layer.

Or, the syringe barrel 268 shown in FIG. 11 can be made from the outside in, for one example, by inserting a first core in the mold cavity, injection molding the outer wall in the mold cavity, then removing the first core from the molded first wall and inserting a second, smaller core, then injection molding the inner wall against the outer wall still residing in the mold cavity. Optionally, a tie layer can be provided to the interior surface of the molded outer wall before over-molding the inner wall onto the tie layer.

Or, the syringe barrel 268 shown in FIG. 11 can be made in a two shot mold. This can be done, for one example, by injection molding material for the inner wall from an inner nozzle and the material for the outer wall from a concentric outer nozzle. Optionally, a tie layer can be provided from a third, concentric nozzle disposed between the inner and outer nozzles. The nozzles can feed the respective wall materials simultaneously. One useful expedient is to begin feeding the outer wall material through the outer nozzle slightly before feeding the inner wall material through the inner nozzle. If there is an intermediate concentric nozzle, the order of flow can begin with the outer nozzle and continue in sequence from the intermediate nozzle and then from the inner nozzle. Or, the order of beginning feeding can start from the inside nozzle and work outward, in reverse order compared to the preceding description.

Optionally, the syringe barrel can be substantially circular and cylindrical at its inner and outer diameters in cross section, particularly at its rear passage 106, to facilitate sealing to vacuum-drawing apparatus, for example the PECVD apparatus described in this specification.

The optional cap 26 is configured to isolate the delivery outlet 34 of the needle 22 from ambient air 50, and can instead or additionally protect a user handling the syringe from accidental needle sticks. The cap 26 as illustrated comprises a lumen 46 having an opening 56 defined by a rim 52. In FIG. 1 the lumen 46 is essentially completely filled by the needle 22 and the tapered nose 110 of the syringe 20. The opening 56 is sized to receive the delivery outlet 34. The rim 52 is seatable against an exterior portion 54 of the barrel.

In the embodiment of FIG. 1, the cap 26 is held in place on the nose 110 of the syringe 20 by a conventional Luer lock arrangement. The tapered nose 110 of the syringe mates with a corresponding tapered throat 112 of the cap 26, and the syringe has a collar 114 with an interior thread 116 receiving the dogs 118 and 120 of the cap 26 to lock the tapered nose and throat 110 and 112 together. The cap 26 can be substantially rigid.

Figure 2:
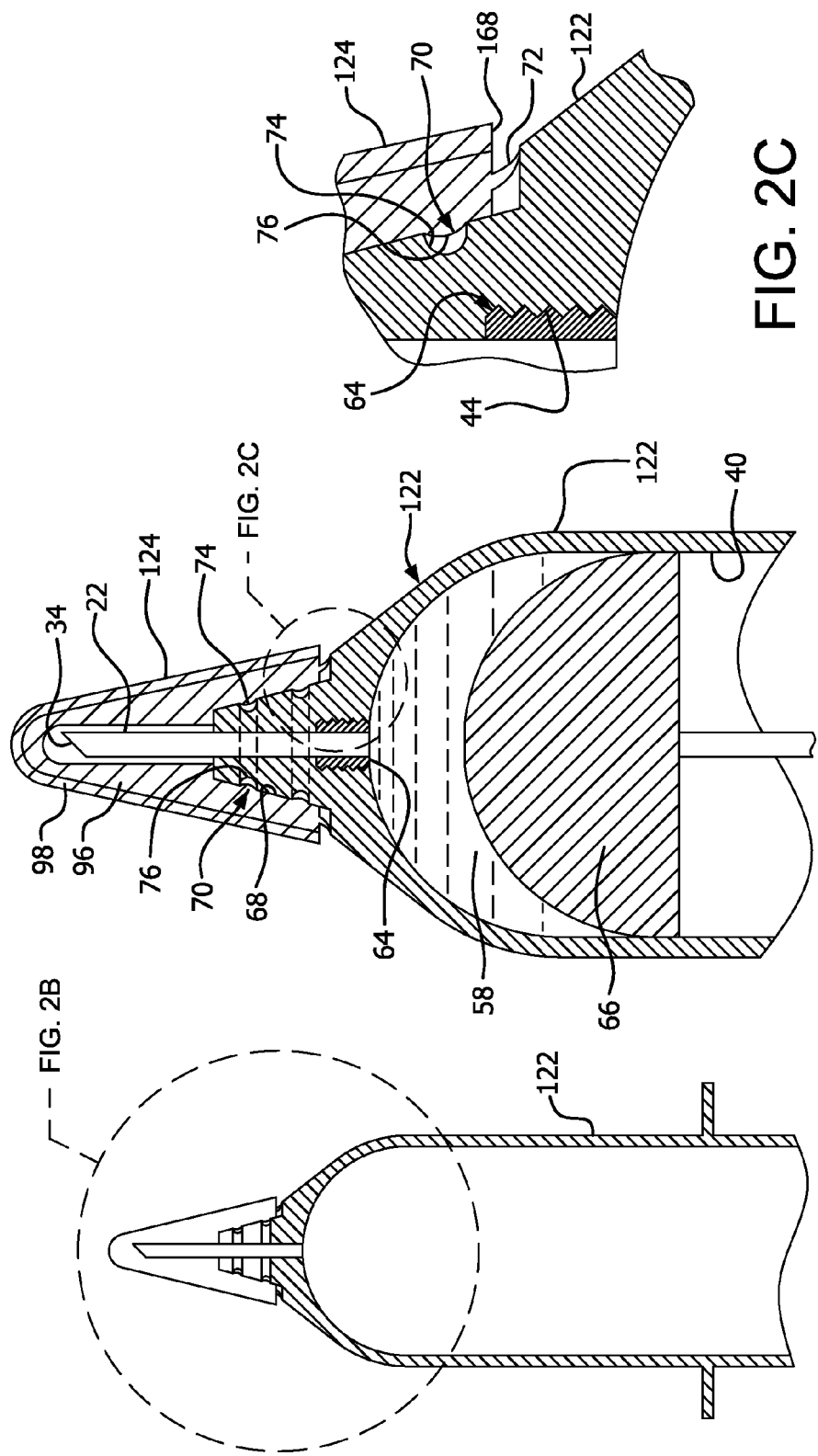

Referring now to FIG. 2, a variation on the syringe barrel 122 and cap 124 is shown. In this embodiment, the cap 124 includes a flexible lip seal 72 at its base to form a moisture-tight seal with the syringe barrel 122.

Optionally in the embodiments of FIGS. 1 and 2, the caps 26 and 124 can withstand vacuum during the PECVD coating process. The caps 26 and 124 can be made of LDPE. Alternative rigid plastic materials can be used as well, for example polypropylene. Additional sealing elements can be provided as well.

Figure 3:
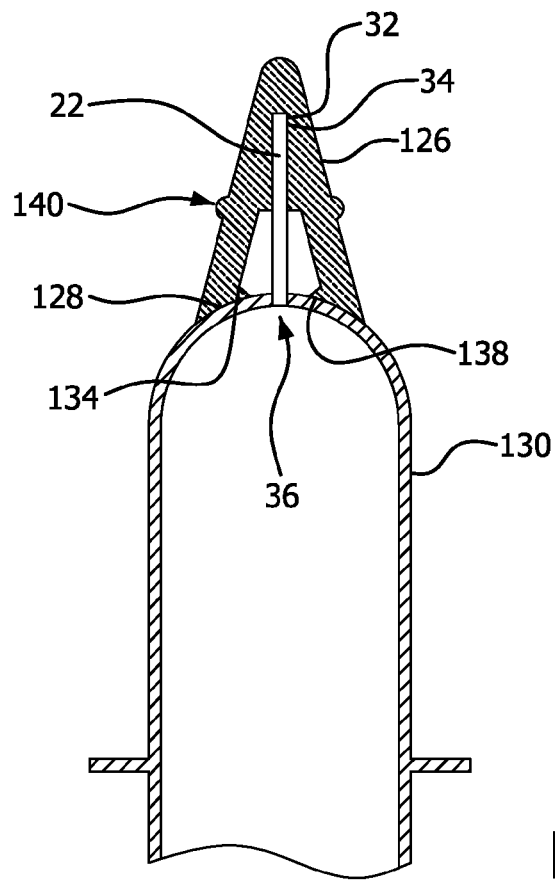
FIG. 3 is a longitudinal section similar to FIG. 1 of another embodiment.

In another option, illustrated in FIG. 3, the cap 126 is flexible, and is designed to seal around the top end of the barrel 130. A deformable material—like a rubber or a thermoplastic elastomer (TPE) can be used for the cap 126.

Preferred TPE materials include fluoroelastomers, and in particular, medical grade fluoroelastomers. Examples include VITON® and TECHNOFLON®. VITON® is preferable in some embodiments. An example of a suitable rubber is EPDM rubber.

During molding, in certain embodiments (illustrated for example in FIG. 3) a small amount of the cap material 132 will be drawn into the tip or delivery outlet 34 of the needle 22 to create a seal. The material 132 should have a durometer such as to permit an appropriate amount of material to be drawn into the needle 22, and to cause the material drawn into the needle 22 to continue to adhere to the cap 126 when it is removed, unplugging the needle 22 for use.

In other embodiments, the cap material can block the delivery outlet 34 of the needle 22 without being drawn into the delivery outlet 34. Suitable material selection to accomplish the desired purposes is within the capabilities of a person of ordinary skill in the art.

An additional seal can be created by coupling an undercut 134 formed in the syringe barrel and projections 138 in the interior of the cap 126, defining a coupling to retain the cap 126. Alternative embodiments can include either one or both of the seals described above.

Optionally, with reference to FIG. 2, the cap 124 can have a base 68 and a coupling 70 configured for securing the cap 26 in a seated position on the barrel. Alternatively or in addition, a flexible lip seal 72 can optionally be provided at the base 68 of the cap 124 for seating against the barrel 122 when the cap 124 is secured on the barrel 122.

Optionally, referring now to FIG. 3, the delivery outlet 34 of the needle 22 can be seated on the cap 126 when the cap 26 is secured on the barrel. This expedient is useful for sealing the delivery outlet 34 against the ingress or egress of air or other fluids, when that is desired.

Optionally, the coupling 70 can include a detent or groove 74 on one of the barrel 122 and the cap 124 and a projection or rib 76 on the other of the barrel 122 and the cap 124, the projection 76 being adapted to mate with the detent 74 when the cap 26 is in its seated position on the barrel. In one contemplated embodiment, a detent 74 can be on the barrel and a projection 76 can be on the cap 26. In another contemplated embodiment, a detent 74 can be on the cap 26 and a projection 76 can be on the barrel. In yet another contemplated embodiment, a first detent 74 can be on the barrel and a first projection 76 mating with the detent 74 can be on the cap 26, while a second detent 75 can be on the cap 26 and the mating second projection 77 can be on the barrel. A detent 74 can be molded in the syringe barrel as an undercut by incorporating side draws such as 92 and 94 in the mold.

The detents 74 mate with the complementary projections 76 to assemble (snap) the cap 26 onto the syringe 20. In this respect the cap 26 is desirably flexible enough to allow sufficient deformation for a snapping engagement of the detents 74 and projections 76.

The caps such as 26, 124, and 126 can be injection molded or otherwise formed, for example from thermoplastic material. Several examples of suitable thermoplastic material are a polyolefin, for example a cyclic olefin polymer (COP), a cyclic olefin copolymer (COC), polypropylene, or polyethylene. The cap 26 can contain or be made of a thermoplastic elastomer (TPE) or other elastomeric material. The cap 26 can also be made of polyethylene terephthalate (PET), polycarbonate resin, or any other suitable material. Optionally, a material for the cap 26 can be selected that can withstand vacuum and maintain sterility within the syringe 20.

Optionally, finger grips 140 (FIG. 3) can be provided on any embodiment of the cap to facilitate easy removal of the cap from the syringe and prevent accidental needle sticks.

Referring to FIG. 1, but optionally for any embodiment, a barrier layer (also sometimes known as a barrier coating) 28 can be provided on at least the hemispheric interior surface portion 42 of the barrel. Optionally, the barrier coating 28 extends over at least a portion of the generally cylindrical interior surface portion 40 of the barrel. Optionally, the barrier coating 28 forms a barrier between the base 36 of the needle 22 and the generally cylindrical interior surface portion 40 of the barrel. Optionally, the barrier coating 28 comprises $SiO_x$, in which x is from about 1.5 to about 2.9. Optionally, the barrier coating 28 is from 1 to 100 nm thick. Optionally, the barrier coating 28 is effective to provide an oxygen barrier.

Optionally, the syringe 20 is prefilled with a fluid 58 and the barrier coating 28 is effective to at least reduce leaching of the material 60 of the barrel into the fluid 58. A barrier coating 28 can also be used in an empty syringe to reduce leaching of the fluid put into the syringe 20 by the end user.

Optionally, the syringe 20 of any embodiment, instead of or in addition to a barrier coating 28, can have a lubricity coating 30 on at least a portion of the generally cylindrical interior surface portion 40 of the barrel. Optionally, the lubricity coating or layer 30 is applied by PECVD. A "lubricity layer" or any similar term is generally defined as a coating that reduces the frictional resistance of the coated surface, relative to the uncoated surface. If the coated object is a syringe (or syringe part, e.g. syringe barrel) or any other item generally containing a plunger or movable part in sliding contact with the coated surface, the frictional resistance has two main aspects—breakout force and plunger sliding force.

The plunger sliding force test is a specialized test of the coefficient of sliding friction of the plunger within a syringe, accounting for the fact that the normal force associated with a coefficient of sliding friction as usually measured on a flat surface is addressed by standardizing the fit between the plunger or other sliding element and the tube or other vessel within which it slides. The parallel force associated with a coefficient of sliding friction as usually measured is comparable to the plunger sliding force measured as described in this specification. Plunger sliding force can be measured, for example, as provided in the ISO 7886-1:1993 test.

The plunger sliding force test can also be adapted to measure other types of frictional resistance, for example the friction retaining a stopper within a tube, by suitable variations on the apparatus and procedure. In one embodiment, the plunger can be replaced by a closure and the withdrawing force to remove or insert the closure can be measured as the counterpart of plunger sliding force.

Also or instead of the plunger sliding force, the breakout force can be measured. The breakout force is the force required to start a stationary plunger moving within a syringe barrel, or the comparable force required to unseat a seated, stationary closure and begin its movement. The breakout force is measured by applying a force to the plunger that starts at zero or a low value and increases until the plunger begins moving. The breakout force tends to increase with storage of a syringe, after the prefilled syringe plunger has pushed away the intervening lubricant or adhered to the barrel due to decomposition of the lubricant between the plunger and the barrel. The breakout force is the force needed to overcome "sticktion," an industry term for the adhesion between the plunger and barrel that needs to be overcome to break out the plunger and allow it to begin moving.

Some utilities of coating a vessel in whole or in part with a lubricity layer, such as selectively at surfaces contacted in sliding relation to other parts, is to ease the insertion or removal of a stopper or passage of a sliding element such as a piston or plunger in a syringe. Applying a lubricity layer by PECVD can avoid or reduce the need to coat the vessel wall or closure with a sprayed, dipped, or otherwise applied organosilicon or other lubricant that commonly is applied in a far larger quantity than would be deposited by a PECVD process.

The coating optionally can be applied to the substrate at a thickness of 1 to 5000 nm, or 10 to 1000 nm, or 10-200 nm, or 20 to 100 nm thick. The thickness of this and other coatings can be measured, for example, by transmission electron microscopy (TEM).

Referring to FIG. 2, anchoring features can be provided along the base of the needle 22 to facilitate good bonding between the plastic syringe and the needle during the molding process. For example, the outside surface 32 of the needle 22 of any embodiment can have a non-cylindrical or flattened portion 64 within at least a portion of the front passage 44 for anchoring the needle within the barrel 122. The non-cylindrical or flattened portion 64 optionally can be provided by machining or tooling an initially cylindrical needle blank. The non-cylindrical or flattened portion optionally can be provided by attaching an initially separate non-cylindrical or flattened portion, as by welding, gluing, or stamping the needle blank and another part together.

Optionally, the syringe 20 of any embodiment can include a plunger 66 sized and positioned to at least substantially seal against and move along the generally cylindrical interior surface portion 40 of the barrel 122. As is well known, a plunger such as plunger 66 is conventionally provided for drawing fluid 58 into the barrel 122 through the delivery outlet 34, and/or for expelling fluid 58 from the delivery outlet 34 of the needle 22. The plunger such as 66 can also seal against the generally cylindrical interior surface portion 40 of the barrel 122 to isolate the fluid 58 in the syringe from the surrounding air, moisture, and other ambient materials and conditions.

Figure 4:
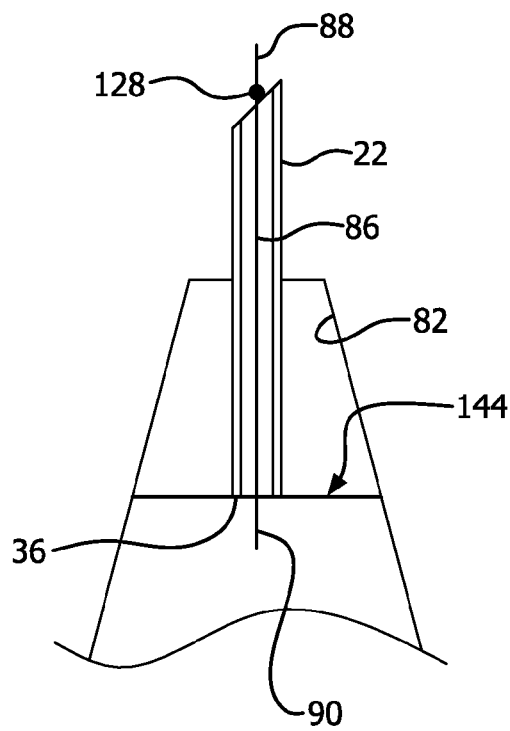
FIG. 4 is a diagrammatic view showing a flexible diaphragm to which the needle 22 is attached.

FIG. 4 is a schematic view showing another embodiment in which a diaphragm 144, which alternatively can be a screen or other pattern of strands defining a central opening, supports the hypodermic needle 22 partially within the mold cavity 82. A strand 86 is inserted in the needle 22 during molding to maintain a clear passage through the needle 22 when the barrel is molded onto the needle 22. The material to be molded can be inserted through gates on each side of the diaphragm 144, or alternatively through openings in the diaphragm or other structure 144. Optionally, the diaphragm 144 can be captured in the molded part. The strand 86 can be removable after molding, as by pulling on the attachment point 128, optionally when withdrawing one part of the mold with respect to another.

Figure 5:
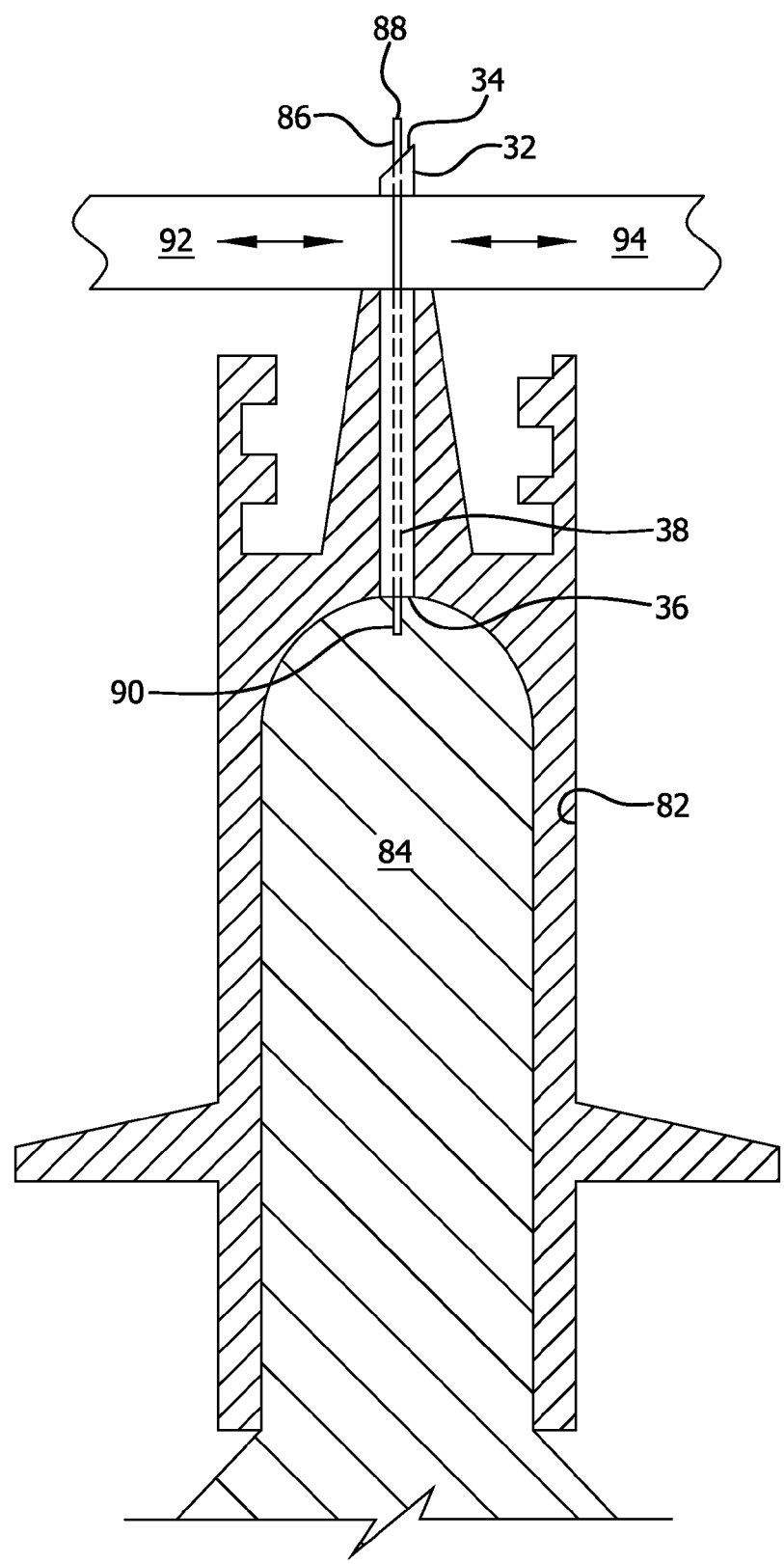
FIG. 5 is a sectional view of a mold cavity and core contemplated for forming the syringe body and staked needle shown in FIG. 1.
Figure 6:
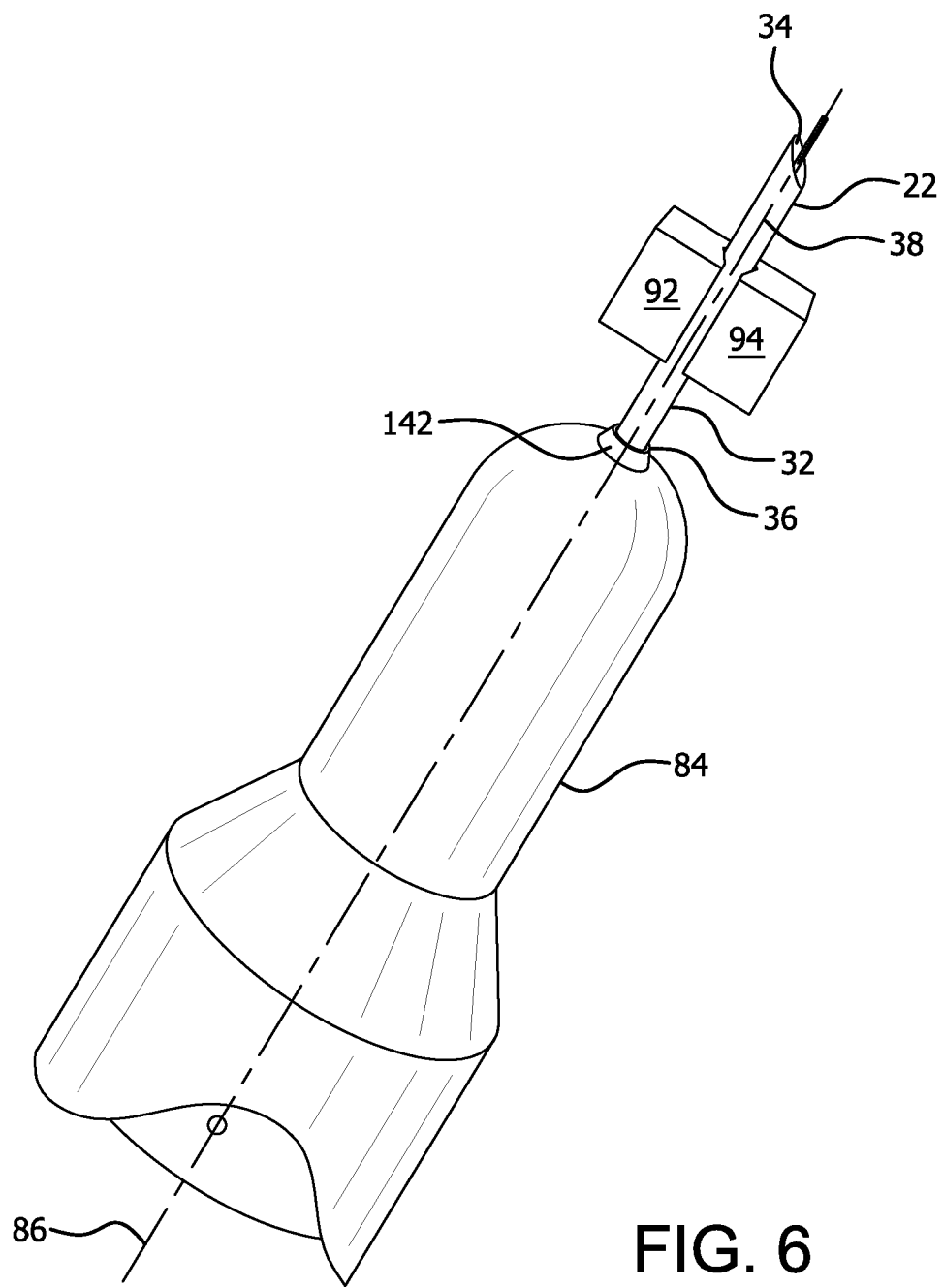
FIG. 6 is a perspective view showing a detail of the core of FIG. 5.

Referring to FIGS. 1, 5, and 6, another aspect of the technology disclosed here is a method of making a syringe 20 with an integrated, staked needle 22 by injection molding at least a portion of the barrel around the needle 22 to secure and seal the needle 22 in place. At least a portion of the needle 22 is inserted into the mold prior to injecting the plastic or other material to form the syringe body. As the plastic cools in the mold cavity, the plastic syringe body bonds to the needle and forms a permanent attachment between the needle and the syringe. The bond between the needle and the syringe optionally is moisture tight, liquid tight, sufficient to maintain sterility, and can hold a vacuum.

A needle 22 is provided having an outside surface 32, a delivery outlet 34 at one end, a base 36 at the other end, and an internal passage 38 extending from the base 36 to the delivery outlet 34.

A mold 80 is provided comprising a mold core 84 and a mold cavity 82 for making a barrel. The barrel the mold 80 is configured to form has a generally cylindrical interior surface portion 40 defining a lumen 48 and a front passage 44.

The needle 22 is flush with the interior surface of the syringe 20. See FIG. 1. This is accomplished by positioning the needle 22 within the mold cavity 82, with its base 36 at a "bottomed out" position abutting the mold core 84 (forming the lumen 48 of the syringe) and at least a portion of its outside surface 32 exposed within the mold cavity 82. The mold core 84 optionally can be adjusted to compensate for shrinkage of the molding material, for example by adding a needle support projection, such as a pin 142. The projection 142 is located at the top of the core where the core contacts the bottom of the needle, to displace the needle upward (with reference to the needle orientation in the Figures), and can be adjusted in size, such as by grinding, to put it at a location that will be flush with the hemispherical surface 42 of the syringe barrel after shrinkage of the molding material.

The barrel is then injection molded by injecting moldable material 60 into the mold cavity 82, forming the portion of the barrel defining the front opening against the portion of the needle 22 outside surface 32 exposed within the mold cavity 82 to join the barrel and the needle 22. Note that FIGS. 5 and 6 are diagrammatic. Additional details such as parting lines and a multi-part mold 80 allowing the syringe body 24 to be released from the mold 80 can be provided by a person skilled in the art.

Optionally, the needle 22 can be held in place and kept clear of molding material during the molding step by threading the internal passage 38 of the needle 22 with a flexible strand 86 having first and second ends 88 and 90. The strand 86 can be any one or more thin filaments or rods of suitable material, without limits on the material from which it is manufactured. For several non-limiting examples, the strand 86 can be a metal wire, a carbon fiber or a glass fiber. The strand material preferably has a melting or glass transition temperature well above the molding temperature. The strand can be incorporated into the mold cavity 82 or core 84, extend into the needle 22, and be held in place outside of the internal passage 38 after the syringe barrel is formed. Release and removal of the mold 80 pulls the strand 86 out from the needle.

The strand 86 can be threaded into the internal passage 38 before injecting moldable material 60 into the mold cavity 82. The strand 86 also can be threaded into a portion of the internal passage 38 of the needle 22. For example, a strand 86 can be threaded into a portion of the internal passage 38 adjacent to the base 36. For another example, a strand 86 can be threaded in to a portion of the internal passage 38 adjacent the delivery outlet 34.

Optionally, the first end 88 of the strand 86 is secured to the mold core 84. Optionally, the second end 90 of the strand 86 is also or instead secured to the mold cavity 82.

Optionally, the needle 22 can be kept clear of molding material during the molding step by providing at least one side draw 92 or 94 associated with the mold cavity 82 and abutting a portion of the outside surface 32 of the needle 22 which will be exposed in the finished syringe 20. The side draw 92 can be configured and positioned to keep the barrel material 60 away from the abutted portion of the outside surface 32 of the needle 22. The side draw, and here a pair of side draws 92 and 94, can be provided and moved into place before injecting moldable material 60 into the mold cavity 82.

Optionally, at least one side draw 92 or 94, and here both, can be used to position the needle 22 in the mold 80. The side draws also can function to form the retaining detents 74. The parting line for the side draws should be in a noncritical region—preferably between the retaining clips and flexible lip, as shown in FIG. 2, but can also be located in other areas displaced from these portions of the cap 26.

Optionally, the cap 26 can be over-molded on the syringe 20. In an embodiment, the cap 26 can be configured to isolate the delivery outlet 34 of the needle 22 from ambient air 50. In an embodiment, the cap 26 can be over-molded into contact with at least the delivery outlet 34 of the needle 22. In an embodiment, the cap 26 can be over-molded from a thermoplastic elastomer.

As another option, shown in FIG. 2 but applicable to any embodiment, the cap 26 can include an internal portion 96 and an external portion 98. The internal portion 96 can be molded out of contact with the syringe barrel. The internal portion 96 can be assembled with the syringe barrel. With the internal portion 96 in place, additional resin defining the external portion 98 of the cap 26 can be over-molded over the internal portion 96 of the cap 26. Optionally, the external and internal portions 98 and 96 of the cap 26 can be integrally joined by the over-molding.

Optionally, a two-shot injection molding process is contemplated. The first shot can be carried out by injecting moldable material 60 into the mold cavity 82, forming the barrel with a staked needle 22. The second shot can be carried out by over-molding a cap 26 on the syringe 20. Shrinkage of the cap during molding can be used to enhance its seal on the syringe 20.

Another two-shot option can be carried out by forming the cap 26 in the first shot and the syringe barrel in the second shot. In this option, the needle 22 can be inserted in the mold cavity 82 before the first shot, the cap 26 can be molded about a portion of the needle 22 including the delivery outlet 34 in the first shot, and the just-molded cap 26 can locate the needle 22 in the mold cavity 82 and expose the base 36 of the needle as the barrel is molded in the second shot.

Alternatively, the syringe 20 alone can be produced using a one-shot molding process without the cap. The cap, if desired, can then be produced separately. A one-shot molding process is particularly useful for syringes having smaller needles, such as for insulin administration.

After joining the barrel and the needle 22, the barrel can be plasma treated. The design of a syringe 20 with a preassembled needle 22 as illustrated facilitates coating the interior surfaces such as 40 and 42 of the syringe barrel using a PECVD process. For this aspect of the invention, the needle 22 alternatively could be preassembled conventionally, as by being glued into the syringe, instead of being staked in the molding process. The following design elements in the syringe 20 are contemplated to be beneficial for efficient PECVD coating. First, the "capillary region" at the needle end of a conventional syringe barrel can be reduced or eliminated, as by making the base 36 of the needle 22 flush with the hemispherical surface portion 42 of the barrel. The capillary region of a conventional syringe has a substantially smaller diameter than the syringe barrel. It is difficult to coat the capillary region of a conventional syringe. The hemispherical surface portion 42 of the barrel, in contrast to a conventional capillary region, is straightforward to coat using PECVD apparatus of the type generally adapted to coat the inside walls of a conventional round-ended medical sample collection tube, sometimes referred to as a test tube.

It is also useful in certain embodiments to assemble the cap 26 on the syringe 20 before PECVD coating the interior surface portions 40 and 42 of the syringe barrel. The cap 26 can be used to seal off or isolate the needle end of the syringe 20, and more precisely the delivery outlet 34 at the inner diameter of the needle 22, from ambient air during PECVD. This expedient can be used to draw a vacuum in the syringe 20, to apply the PECVD coating, without putting the syringe 20 in a separate vacuum chamber.

Suitable apparatus for PECVD coating the interior walls of a vessel, such as the interior surface portions 40 and 42 of the syringe barrel, is illustrated generally by FIGS. 7-10.

Figure 7:
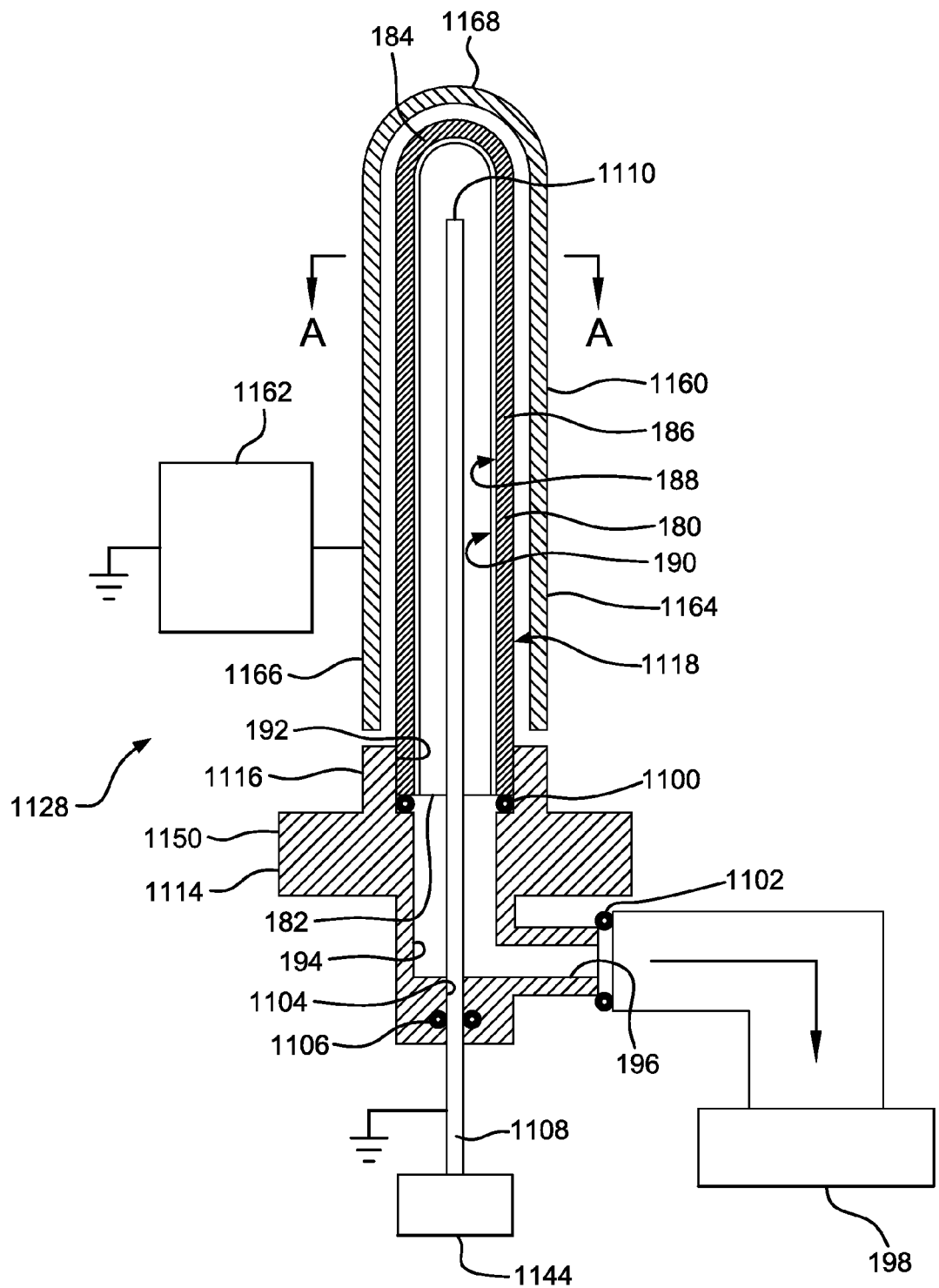
FIG. 7 is a longitudinal section of apparatus contemplated for PECVD treatment of the syringe of FIG. 1 or other vessels. Treatment of a blood collection tube is specifically illustrated in FIG. 7.

FIG. 7 shows a vessel holder 1150 having a vessel port 182 configured to receive and seat the opening of a vessel 180, for example the back opening 106 of the syringe 20 of FIG. 1 (i.e. substituting the syringe barrel of FIG. 1, with the needle 22 and the cap 26 intact, for the vessel 180 and configuring the electrode 1160, as by providing a U-section tunnel electrode 1160, to pass the syringe barrel and attached needle 22 and cap 26 in close proximity to the electrode 1160).

The interior surface of a seated vessel 180 or 24 can be processed via the vessel port 182. The vessel holder 1150 can include a duct, for example a vacuum duct 1194, for withdrawing a gas from a vessel 180 seated on the vessel port 192. The vessel holder can include a second port, for example a vacuum port 196 communicating between the vacuum duct 194 and an outside source of vacuum, such as the vacuum pump 198. The vessel port 192 and vacuum port 196 can have sealing elements, for example O-ring butt seals, respectively 1100 and 1102, or side seals between an inner or outer cylindrical wall of the vessel port 182 and an inner or outer cylindrical wall of the vessel 180 to receive and form a seal with the vessel 180 or outside source of vacuum 198 while allowing communication through the port. Gaskets or other sealing arrangements can or also be used.

The vessel holder such as 1150 can be made of any material, for example thermoplastic material and/or electrically nonconductive material. Or, the vessel holder such as 1150 can be made partially, or even primarily, of electrically conductive material and faced with electrically nonconductive material, for example in the passages defined by the vessel port 192, vacuum duct 194, and vacuum port 196. Examples of suitable materials for the vessel holder 1150 are: a polyacetal, for example Delrin® acetal material sold by E. I. du Pont De Nemours and Company, Wilmington Del.; polytetrafluoroethylene (PTFE), for example Teflon® PTFE sold by E. I. du Pont De Nemours and Company, Wilmington Del.; Ultra-High-Molecular-Weight Polyethylene (UHMWPE); High density Polyethylene (HDPE); or other materials known in the art or newly discovered.

FIG. 7 also illustrates that the vessel holder, for example 1150, can have a collar 1116 for centering the vessel 180 when it is approaching or seated on the port 192.

Figure 8:
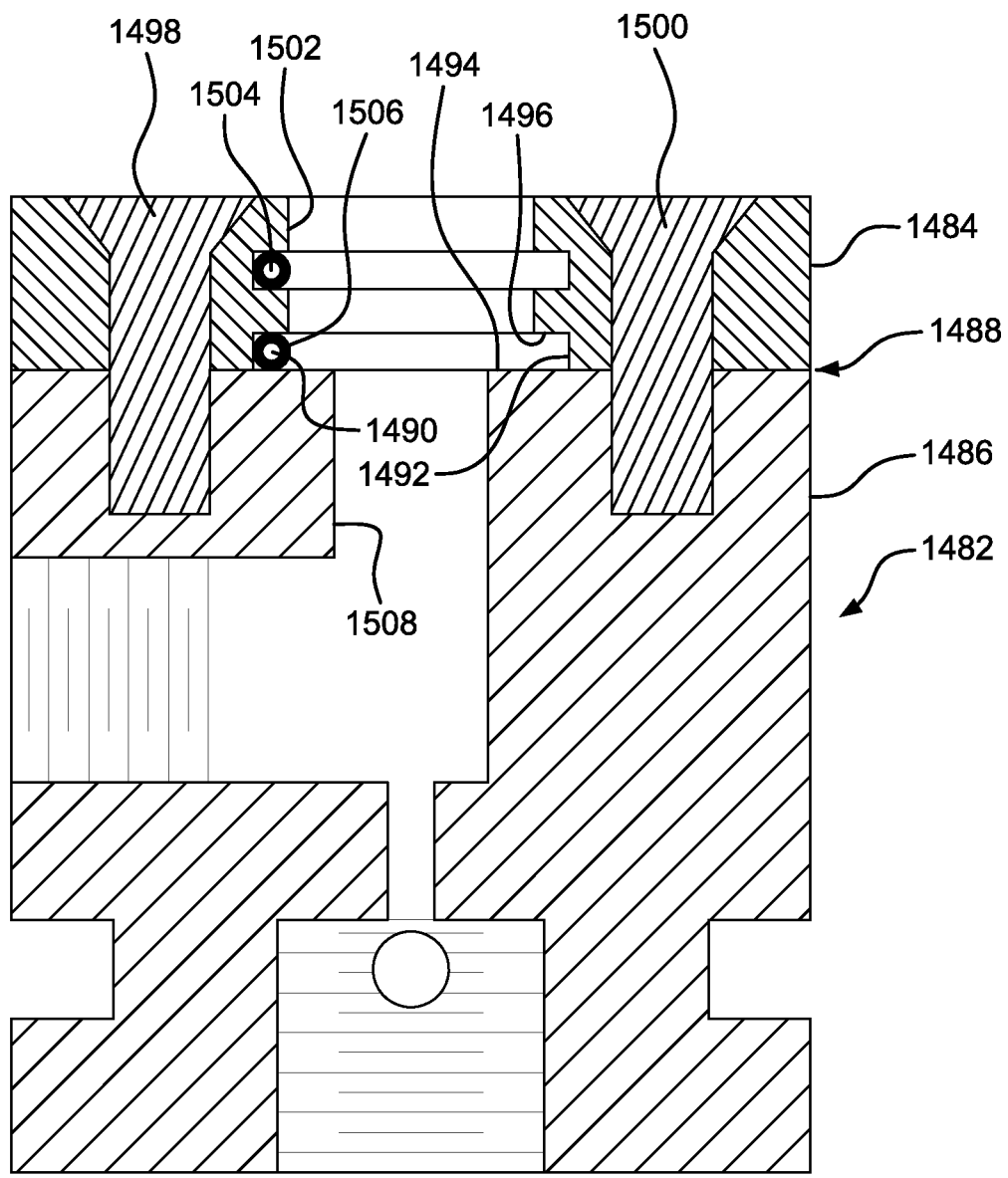
FIG. 8 is a longitudinal section of an alternative vessel holder that can be substituted for the vessel holder of FIG. 7.

FIG. 8 is an alternative construction for a vessel holder 1482 particularly suited to receive a vessel like the syringe 20 having a tube-like back opening 106, as illustrated in FIG. 1. The vessel holder 1482 comprises an upper portion 1484 and a base 1486 joined together at a joint 1488. A sealing element, for example an O-ring 1490 (the right side of which is cut away to allow the pocket retaining it to be described) is captured between the upper portion 1484 and the base 1486 at the joint 1488. In the illustrated embodiment, the O-ring 1490 is received in an annular pocket 1492 to locate the O-ring when the upper portion 1484 is joined to the base 1486.

In this embodiment, the O-ring 1490 is captured and bears against a radially extending abutment surface 1494 and the radially extending wall 1496 partially defining the pocket 1492 when the upper portion 1484 and the base 1486 are joined, in this case by the screws 1498 and 1500. The O-ring 1490 thus seats between the upper portion 1484 and base 1486. The O-ring 1490 captured between the upper portion 1484 and the base 1486 also receives the vessel 180 (removed in this figure for clarity of illustration of other features) and forms a first O-ring seal of the vessel port 1502 about the vessel 180 opening.

In this embodiment, though not a requirement, the vessel port 1502 has both the first O-ring 1490 seal and a second axially spaced O-ring 1504 seal, each having an inner diameter such as 1506 sized to receive the outer diameter of a vessel such as 180 for sealing between the vessel port 1502 and a vessel such as 180. The spacing between the O-rings 1490 and 1504 provides support for a vessel such as 180 at two axially spaced points, preventing the vessel such as 180 from being skewed with respect to the O-rings 1490 and 1504 or the vessel port 1502. In this embodiment, though not a requirement, the radially extending abutment surface 1494 is located proximal of the O-ring 1490 and 1506 seals and surrounding the vacuum duct 1508.

The cap 26 can directly seal the delivery outlet 34 of the needle 22. As explained in this specification, at least the portion of the cap 26 adjacent to the delivery outlet 34 be a TPE that compresses and forms a seal at the end of the needle (flexible cap embodiment). OR the cap can be placed over the needle 22 and seal along the syringe 20. In this embodiment, it may be useful that the cap be or include a substantially rigid shell to withstand deformation due to the vacuum.

Optionally, as shown in FIG. 1, a permanent cap 26 equipped with a mating Luer coupling and suitable for protecting the needle 22 before use can be installed on the syringe 20 over the needle 22 before conducting PECVD. In another variation of this process, a special cap can be attached to the syringe for the purpose of facilitating PECVD, and optionally replaced with a conventional cap for downstream handling and use of the syringe 20.

The barrel can be plasma treated, for example using PECVD, by forming a plasma 100 within the lumen 48 of the barrel, introducing an organosilicon gas 102 within the lumen 48 of the barrel, and depositing a coating 28 or 30 of a nongas organosilicon material on at least one of the generally cylindrical interior surface portion 40 and the generally hemispherical interior surface portion 42 of the barrel. Using plasma treatment or other methods, the coating 28 or 30 of a nongas organosilicon material can be deposited between the base 36 of the needle 22 and the barrel.

The precursor for the PECVD coating of the present invention is broadly defined as an organometallic precursor. An organometallic precursor is defined in this specification as comprehending compounds of metal elements from Group III and/or Group IV of the Periodic Table having organic residues, e.g. hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Indium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having at least one of the linkages:

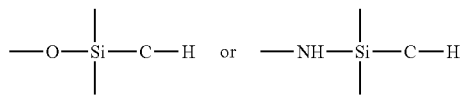

The first structure immediately above is a tetravalent silicon atom connected to an oxygen atom and an organic carbon atom (an organic carbon atom being a carbon atom bonded to at least one hydrogen atom). The second structure immediately above is a tetravalent silicon atom connected to an —NH— linkage and an organic carbon atom (an organic carbon atom being a carbon atom bonded to at least one hydrogen atom). Optionally, the organosilicon precursor is selected from the group consisting of a linear siloxane, a monocyclic siloxane, a polycyclic siloxane, a polysilsesquioxane, a linear silazane, a monocyclic silazane, a polycyclic silazane, a polysilsesquiazane, and a combination of any two or more of these precursors. Also contemplated as a precursor, though not within the two formulas immediately above, is an alkyl trimethoxysilane.

In particular, the organosilicon precursor can be a monocyclic siloxane, preferably OMCTS.

As described above, the organosilicon precursor can also be a linear siloxane, preferably HMDSO. If an oxygen-containing precursor (e.g. a siloxane) is used, a representative predicted empirical composition resulting from PECVD under conditions forming a hydrophobic or lubricating coating would be $Si_wO_xC_yH_z$ as defined in the Definition Section, while a representative predicted empirical composition resulting from PECVD under conditions forming a barrier coating would be $SiO_x$, where x in this formula is from about 1.5 to about 2.9. If a nitrogen-containing precursor (e.g. a silazane) is used, the predicted composition would be $Si_wN_xC_yH_z$, i.e. in $Si_wO_xC_yH_z$ as specified in the Definition Section, O is replaced by N and the indices are adapted to the higher valency of N as compared to O (3 instead of 2). The latter adaptation will generally follow the ratio of w, x, y and z in a siloxane to the corresponding indices in its aza counterpart. In a particular aspect of the invention, $Si_{w*}$—$N_{x*}$—$C_{y*}$—$H_{z*}$ in which w*, x*, y*, and z* are defined the same as w, x, y, and z for the siloxane counterparts, but for an optional deviation in the number of hydrogen atoms.

One type of precursor starting material having the above empirical formula is a linear siloxane, for example a material having the following formula:

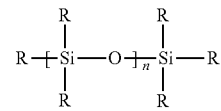

in which each R is independently selected from alkyl, for example methyl, ethyl, propyl, isopropyl, butyl, isobutyl, t-butyl, vinyl, alkyne, or others, and n is 1, 2, 3, 4, or greater, optionally two or greater. Several examples of contemplated linear siloxanes are
  hexamethyldisiloxane (HMDSO),
  octamethyltrisiloxane,
  decamethyltetrasiloxane,
  dodecamethylpentasiloxane,
or combinations of two or more of these. The analogous silazanes in which —NH— is substituted for the oxygen atom in the above structure are also useful for making analogous coatings. Several examples of contemplated linear silazanes are octamethyltrisilazane, decamethyltetrasilazane, or combinations of two or more of these.

V.C. Another type of precursor starting material is a monocyclic siloxane, for example a material having the following structural formula:

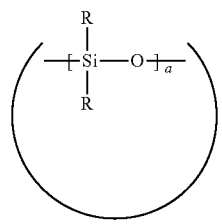

in which R is defined as for the linear structure and "a" is from 3 to about 10, or the analogous monocyclic silazanes. Several examples of contemplated hetero-substituted and unsubstituted monocyclic siloxanes and silazanes include 1,3,5-trimethyl-1,3,5-tris(3,3,3-trifluoropropyl)methyl]cyclotrisiloxane
2,4,6,8-tetramethyl-2,4,6,8-tetravinylcyclotetrasiloxane,
pentamethylcyclopentasiloxane,
pentavinylpentamethylcyclopentasiloxane,
hexamethylcyclotrisiloxane,
hexaphenylcyclotrisiloxane,
octamethylcyclotetrasiloxane (OMCTS),
octaphenylcyclotetrasiloxane,
decamethylcyclopentasiloxane
dodecamethylcyclohexasiloxane,
methyl(3,3,3-trifluoropropl)cyclosiloxane,
Cyclic organosilazanes are also contemplated, such as
Octamethylcyclotetrasilazane,
1,3,5,7-tetravinyl-1,3,5,7-tetramethylcyclotetrasilazane
hexamethylcyclotrisilazane,
octamethylcyclotetrasilazane,
decamethylcyclopentasilazane,
dodecamethylcyclohexasilazane, or
combinations of any two or more of these.

V.C. Another type of precursor starting material is a polycyclic siloxane, for example a material having one of the following structural formulas:

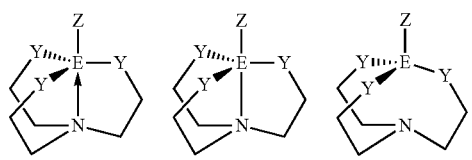

in which Y can be oxygen or nitrogen, E is silicon, and Z is a hydrogen atom or an organic substituent, for example alkyl such as methyl, ethyl, propyl, isopropyl, butyl, isobutyl, t-butyl, vinyl, alkyne, or others. When each Y is oxygen, the respective structures, from left to right, are a silatrane, a silquasilatrane, and a silproatrane. When Y is nitrogen, the respective structures are an azasilatrane, an azasilquasiatrane, and an azasilproatrane.

V.C. Another type of polycyclic siloxane precursor starting material is a polysilsesquioxane, with the empirical formula $RSiO_{1.5}$ and the structural formula:

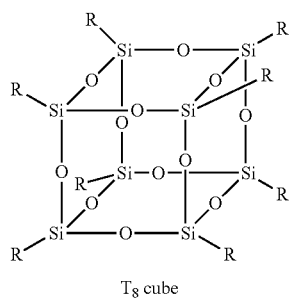

T$_8$ cube in which each R is a hydrogen atom or an organic substituent, for example alkyl such as methyl, ethyl, propyl, isopropyl, butyl, isobutyl, t-butyl, vinyl, alkyne, or others. Two commercial materials of this sort are SST-eM01 poly(methylsilsesquioxane), in which each R is methyl, and SST-3 MH1.1 poly(Methyl-Hydridosilsesquioxane), in which 90% of the R groups are methyl, 10% are hydrogen atoms. This material is available in a 10% solution in tetrahydrofuran, for example. Combinations of two or more of these are also contemplated. Other examples of a contemplated precursor are methylsilatrane, CAS No. 2288-13-3, in which each Y is oxygen and Z is methyl, methylazasilatrane, SST-eM01 poly(methylsilsesquioxane), in which each R optionally can be methyl, SST-3 MH1.1 poly(Methyl-Hydridosilsesquioxane), in which 90% of the R groups are methyl and 10% are hydrogen atoms, or a combination of any two or more of these.

V.C. The analogous polysilsesquiazanes in which —NH— is substituted for the oxygen atom in the above structure are also useful for making analogous coatings. Examples of contemplated polysilsesquiazanes are a poly(methylsilsesquiazane), in which each R is methyl, and a poly(Methyl-Hydridosilsesquiazane, in which 90% of the R groups are methyl, 10% are hydrogen atoms. Combinations of two or more of these are also contemplated.

V.C. One particularly contemplated precursor for the lubricity layer according to the present invention is a monocyclic siloxane, for example is octamethylcyclotetrasiloxane.

One particularly contemplated precursor for the hydrophobic layer according to the present invention is a monocyclic siloxane, for example is octamethylcyclotetrasiloxane.

One particularly contemplated precursor for the barrier coating according to the present invention is a linear siloxane, for example is HMDSO.

V.C. In any of the coating methods according to the present invention, the applying step optionally can be carried out by vaporizing the precursor and providing it in the vicinity of the substrate. E.g., OMCTS is usually vaporized by heating it to about 50° C. before applying it to the PECVD apparatus.

V.2 General PECVD Method

In the context of the present invention, the following PECVD method is generally applied, which contains the following steps:

(a) providing a gaseous reactant comprising a precursor as defined herein, optionally an organosilicon precursor, and optionally $O_2$ in the vicinity of the substrate surface; and (b) generating a plasma from the gaseous reactant, thus forming a coating on the substrate surface by plasma enhanced chemical vapor deposition (PECVD).

In the method, the coating characteristics are advantageously set by one or more of the following conditions: the plasma properties, the pressure under which the plasma is applied, the power applied to generate the plasma, the presence and relative amount of $O_2$ in the gaseous reactant, the plasma volume, and the organosilicon precursor. Optionally, the coating characteristics are set by the presence and relative amount of $O_2$ in the gaseous reactant and/or the power applied to generate the plasma.

In all embodiments of the present invention, the plasma is in an optional aspect a non-hollow-cathode plasma.

In a further preferred aspect, the plasma is generated at reduced pressure (as compared to the ambient or atmospheric pressure). Optionally, the reduced pressure is less than 300 mTorr, optionally less than 200 mTorr, even optionally less than 100 mTorr.

The PECVD optionally is performed by energizing the gaseous reactant containing the precursor with electrodes powered at a frequency at microwave or radio frequency, and optionally at a radio frequency. The radio frequency preferred to perform an embodiment of the invention will also be addressed as "RF frequency". A typical radio frequency range for performing the present invention is a frequency of from 10 kHz to less than 300 MHz, optionally from 1 to 50 MHz, even optionally from 10 to 15 MHz. A frequency of 13.56 MHz is most preferred, this being a government sanctioned frequency for conducting PECVD work.

There are several advantages for using a RF power source versus a microwave source: Since RF operates at lower power, there is less heating of the substrate/vessel. Because the focus of the present invention is putting a plasma coating on plastic substrates, lower processing temperature are desired to prevent melting/distortion of the substrate. To prevent substrate overheating when using microwave PECVD, the microwave PECVD is applied in short bursts, by pulsing the power. The power pulsing extends the cycle time for the coating, which is undesired in the present invention. The higher frequency microwave can also cause offgassing (also known as outgassing) of volatile substances like residual water, oligomers and other materials in the plastic substrate. This offgassing can interfere with the PECVD coating. A major concern with using microwave for PECVD is delamination of the coating from the substrate. Delamination occurs because the microwaves change the surface of the substrate prior to depositing the coating layer. To mitigate the possibility of delamination, interface coating layers have been developed for microwave PECVD to achieve good bonding between the coating and the substrate. No such interface coating layer is needed with RF PECVD as there is no risk of delamination. Finally, the lubricity layer and hydrophobic layer according to the present invention are advantageously applied using lower power. RF power operates at lower power and provides more control over the PECVD process than microwave power. Nonetheless, microwave power, though less preferred, is usable under suitable process conditions.

Furthermore, for all PECVD methods described herein, there is a specific correlation between the power (in Watts) used to generate the plasma and the volume of the lumen wherein the plasma is generated. Typically, the lumen is the lumen of a vessel coated according to the present invention. The RF power should scale with the volume of the vessel if the same electrode system is employed. Once the composition of a gaseous reactant, for example the ratio of the precursor to $O_2$, and all other parameters of the PECVD coating method but the power have been set, they will typically not change when the geometry of a vessel is maintained and only its volume is varied. In this case, the power will be directly proportional to the volume. Thus, starting from the power to volume ratios provided by present description, the power which has to be applied in order to achieve the same or a similar coating in a vessel of same geometry, but different size, can easily be found. The influence of the vessel geometry on the power to be applied is illustrated by the results of the Examples for tubes in comparison to the Examples for syringe barrels.

For any coating of the present invention, the plasma is generated with electrodes powered with sufficient power to form a coating on the substrate surface.

For an oxygen barrier layer, in the method according to an embodiment of the invention the plasma is optionally generated:

(i) with electrodes supplied with an electric power of from 8 to 500 W, optionally from 10 to 400 W, optionally from 20 to 350 W, optionally from 25 to 300 W, optionally from 25 to 50 W, for example; and/or (ii) wherein the ratio of the electrode power to the plasma volume is less than 10 W/ml, optionally is from 5 W/ml to 0.1 W/ml, optionally is from 4 W/ml to 0.1 W/ml, optionally from 2 W/ml to 0.2 W/ml.

(ii) the ratio of the electrode power to the plasma volume is equal or more than 5 W/ml, optionally is from 6 W/ml to 150 W/ml, optionally is from 7 W/ml to 100 W/ml, optionally from 7 W/ml to 20 W/ml.

For a lubricity layer or hydrophobic layer, in the method according to an embodiment of the invention the plasma is optionally generated:

(i) with electrodes powered with sufficient power to form a layer on the substrate surface, optionally with electrodes supplied with an electric power of from 0.1 to 25 W, optionally from 1 to 22 W, optionally from 3 to 17 W, even optionally from 5 to 14 W, optionally from 7 to 11 W, optionally 8 W; and/or (ii) the ratio of the electrode power to the plasma volume is less than 10 W/ml, optionally is from 5 W/ml to 0.1 W/ml, optionally is from 4 W/ml to 0.1 W/ml, optionally from 2 W/ml to 0.2 W/ml.

The vessel geometry can also influence the choice of the gas inlet used for the PECVD coating. In a particular aspect, a syringe can be coated with an open tube inlet, and a tube can be coated with a gas inlet having small holes which is extended into the tube.

The power (in Watts) used for PECVD also has an influence on the coating properties. Typically, an increase of the power will increase the barrier properties of the coating, and a decrease of the power will increase the lubricity and hydrophobicity of the coating. E.g., for a coating on the inner wall of syringe barrel having a volume of about 3 ml, a power of more than 30 W will lead to a coating which is predominantly a barrier coating, while a power of less than 30 W will lead to a coating which is predominantly a lubricity layer (see Examples).

A further parameter determining the coating properties is the ratio of $O_2$ (or another oxidizing agent) to the precursor (e.g. organosilicon precursor) in the gaseous reactant used for generating the plasma. Typically, an increase of the $O_2$ ratio in the gaseous reactant will increase the barrier properties of the coating, and a decrease of the $O_2$ ratio will increase the lubricity and hydrophobicity of the coating.

If a lubricity layer is desired, then $O_2$ is optionally present in a volume-volume ratio to the gaseous reactant of from 0:1 to 5:1, optionally from 0:1 to 1:1, even optionally from 0:1 to 0.5:1 or even from 0:1 to 0.1:1. Most advantageously, essentially no oxygen is present in the gaseous reactant. Thus, the gaseous reactant should comprise less than 1 vol % $O_2$, for example less than 0.5 vol % $O_2$, and optionally is $O_2$-free. The same applies to a hydrophobic layer.

If, on the other hand, a barrier or $SiO_x$ coating is desired, then the $O_2$ is optionally present in a volume:volume ratio to the gaseous reactant of from 1:1 to 100:1 in relation to the silicon containing precursor, optionally in a ratio of from 5:1 to 30:1, optionally in a ratio of from 10:1 to 20:1, even optionally in a ratio of 15:1.

PECVD coating a syringe 20 with a staked needle 22 already in place has process advantages. The needle 22 is an electrically conductive surface in contact with the radio frequency (RF) electric field that generates the plasma. Since the needle is not electrically connected to ground, it is a floating surface within the plasma space. A floating surface acquires a negative charge when in contact with the plasma, creating a potential (electrical) difference between the floating surface and the plasma bulk. The potential difference will help to accelerate ions to the area around the needle opening, ensuring coating coverage up to and including the needle itself.

If the inner diameter of the needle is small, for example less than about 0.5 mm as commonly is the case for medical syringes, and the process occurs at pressures greater than 100 mTorr, as is contemplated in certain embodiments, a plasma will not be ignited within the needle interior.

Addressing the inside or inner diameter, medical needles are produced having a wide variety of gauges, respectively having the inner diameter and other dimensions indicated in Table 1. As will be apparent from Table 1, many smaller-diameter (larger gauge number) needles have an inner diameter less than about 0.5 mm.

TABLE 1

Hypodermic needle sizes.

| Needle Gauge | Nominal Outer Diameter | | Nominal Inner Diameter | | Nominal Wall Thickness | |
|---|---|---|---|---|---|---|
| | inches | mm | inches | mm | inches | mm |
| 7 | 0.180 | 4.572 | 0.150 | 3.810 | 0.015 | 0.381 |
| 8 | 0.165 | 4.191 | 0.135 | 3.429 | " | " |
| 9 | 0.148 | 3.759 | 0.118 | 2.997 | " | " |
| 10 | 0.134 | 3.404 | 0.106 | 2.692 | 0.014 | 0.356 |
| 11 | 0.120 | 3.048 | 0.094 | 2.388 | 0.013 | 0.330 |
| 12 | 0.109 | 2.769 | 0.085 | 2.159 | 0.012 | 0.305 |
| 13 | 0.095 | 2.413 | 0.071 | 1.803 | " | " |
| 14 | 0.083 | 2.108 | 0.063 | 1.600 | 0.01 | 0.254 |
| 15 | 0.072 | 1.829 | 0.054 | 1.372 | 0.009 | 0.229 |
| 16 | 0.065 | 1.651 | 0.047 | 1.194 | " | " |
| 17 | 0.058 | 1.473 | 0.042 | 1.067 | 0.008 | 0.203 |
| 18 | 0.050 | 1.270 | 0.033 | 0.838 | 0.0085 | 0.216 |
| 19 | 0.042 | 1.067 | 0.027 | 0.686 | 0.0075 | 0.191 |
| 20 | 0.03575 | 0.9081 | 0.02375 | 0.603 | 0.006 | 0.1524 |
| 21 | 0.03225 | 0.8192 | 0.02025 | 0.514 | " | " |
| 22 | 0.02825 | 0.7176 | 0.01625 | 0.413 | " | " |
| 22s | " | " | 0.006 | 0.152 | 0.0111 | 0.2826 |
| 23 | 0.02525 | 0.6414 | 0.01325 | 0.337 | 0.006 | 0.1524 |
| 24 | 0.02225 | 0.5652 | 0.01225 | 0.311 | 0.005 | 0.1270 |
| 25 | 0.02025 | 0.5144 | 0.01025 | 0.260 | " | " |
| 26 | 0.01825 | 0.4636 | " | " | 0.004 | 0.1016 |
| 26s | 0.01865 | 0.4737 | 0.005 | 0.127 | 0.0068 | 0.1734 |
| 27 | 0.01625 | 0.4128 | 0.00825 | 0.210 | 0.004 | 0.1016 |
| 28 | 0.01425 | 0.3620 | 0.00725 | 0.184 | 0.0035 | 0.0889 |
| 29 | 0.01325 | 0.3366 | " | " | 0.003 | 0.0762 |
| 30 | 0.01225 | 0.3112 | 0.00625 | 0.159 | " | " |
| 31 | 0.01025 | 0.2604 | 0.00525 | 0.133 | 0.0025 | 0.0635 |
| 32 | 0.00925 | 0.2350 | 0.00425 | 0.108 | " | " |
| 33 | 0.00825 | 0.2096 | " | " | 0.002 | 0.0508 |
| 34 | 0.00725 | 0.1842 | 0.00325 | 0.0826 | " | " |

The process pressure can be controlled and adjusted as necessary to ensure that the inside of the needle 22 is not coated. Only the outside surface 32 of the needle (including the base) will be coated under these conditions. Additionally, any potential gaps around the needle will also be coated, providing a near hermetic seal between the needle 22 and the barrel.

The PECVD coating process can be similar to the coating process for a conventional syringe. The main difference between coating a syringe with a needle, versus a syringe without a needle, is that there is no requirement to flow the gas up and into the capillary area defining the front passage 44 of the syringe barrel if a needle is already in place. Furthermore, the presence of the needle itself will help to insure that the plasma is uniform in the area around the needle. Lastly, the gas inlet will most likely be the same in both cases. For example, the gas inlet for a syringe can be an electrically conductive metal tube having an outside diameter of ⅛ in. (3.2 mm) and an inside diameter of 1/16 in. (1.6 mm) centered in and extending 20 mm into the rear passage 106 of the syringe barrel.

The organosilicon material coating 28 can comprise SiOx, in which x is from about 1.5 to about 2.9. The organosilicon material coating can also or instead comprise a lubricity coating 30.

In the present method the base 36 of the needle 22 is positioned within the mold cavity 82 at least substantially flush with the mold core 84.

The materials and construction of the needle 22, barrel, and cap 26 formed in the method can be those previously described. The plunger 68 can be made of the same material as the barrel or other materials, and conventionally has a tip 104 made of elastomeric material to seal the fluid 58 within the barrel after the syringe is filled.

Working Examples

Example 1

Gas Barrier Coating (SiO$_x$)

An injection molded COO syringe is interior coated with SiOx after the needle is molded into the syringe as described in this specification.

The apparatus as shown in FIG. 7 with the sealing mechanism of FIG. 8 is modified to hold the syringe 20 of FIG. 1 with sealing at the rear passage 106 of the syringe and with a needle 22 already in place. A temporary cap is fabricated out of a stainless steel Luer fitting 1334 secured to the neck of a polypropylene vessel 1296 to receive the Luer fitting 108 of the syringe barrel and seal the delivery outlet 34 of the syringe barrel, (See FIGS. 9 and 10) allowing the interior or lumen 48 of the syringe barrel to be evacuated. The polypropylene vessel 1296 is sized to receive the needle 22.

The vessel holder 1484 (upper portion), 1486 (base portion) is made from Delrin™ with an outer diameter of 1.75 in. (44 mm) and a height of 1.75 in. (44 mm). The vessel holder is housed in a Delrin structure that allows the device to move in and out of the electrode (1168).

The electrode is made from copper with a Delrin shield. The Delrin shield is conformal around the outside of the copper electrode. The electrode measures approximately 3 in. (76 mm) high (inside) and is approximately 0.75 in. (19 mm) wide.

The COO syringe is inserted into the vessel holder base sealing with Viton O-rings around the bottom of the flat section of the syringe.

The COO syringe is carefully moved into the sealing position over the extended (stationary) ⅛ in. (approximately 3 mm) diameter brass gas inlet and pushed against a copper plasma screen. The copper plasma screen is a perforated copper foil material (K&S Engineering Part #LXMUW5 Copper mesh) cut to fit the outer diameter of the COO syringe and is held in place by a small ledge that acts as a stop for the COO syringe insertion. Two pieces of the copper mesh are fit snugly around the brass gas inlet insuring good electrical contact. The brass inlet extends approximately 20 mm into the interior of the COO syringe and is open at its end.

The gas inlet extends through a Swagelok fitting located at the bottom of the vessel holder, extending through the vessel holder base structure. The gas inlet is grounded to the casing of the RF matching network. The gas inlet is connected to a stainless steel assembly comprised of Swagelok fittings incorporating a manual ball valve for venting, a thermocouple pressure gauge and a bypass valve connected to the vacuum pumping line. In addition, the gas system is connected to the gas inlet allowing the process gases, oxygen and hexamethyldisiloxane (HMDSO), to be flowed through the gas inlet (under process pressures) into the interior of the COO syringe.

The gas system includes a Aalborg GFC17 mass flow meter (Cole Parmer Part # EW-32661-34) for controllably flowing oxygen at 90 sccm into the process and a PEEK capillary (outer diameter OD 1/16 in. (approximately 16 mm), inner diameter ID 0.004 in. (approximately 0.1 mm)) of length 49.5 in. (approximately 126 cm). The PEEK capillary end is inserted into liquid Hexamethyldisiloxane (HMDSO) (Alfa Aesar Part Number L16970, NMR Grade). The liquid HMDSO is pulled through the capillary due to the lower pressure in the COO syringe during processing. The HMDSO is then vaporized into a vapor at the exit of the capillary as it enters the low pressure region. To ensure no condensation of the liquid HMDSO past this point, the gas stream (including the oxygen) is diverted to the pumping line when it is not flowing into the interior of the COO syringe for processing via a Swagelok 3-way valve.

Once the COO syringe is installed, the vacuum pump valve is opened to the vessel holder and the interior of the syringe. An Alcatel rotary vane vacuum pump and blower comprises the vacuum pump system. The pumping system allows the interior of the syringe to be reduced to pressure(s) of less than 150 mTorr. Once the base vacuum level is achieved, the vessel holder assembly is moved into the electrode assembly. The gas stream (oxygen and HMDSO vapor) is flowed into the brass gas inlet (by adjusting the 3-way valve from the pumping line to the gas inlet). Pressure inside of the COO syringe is approximately 200 mTorr as measured by a capacitance manometer (MKS) installed on the pumping line near the valve that controlled the vacuum. In addition to the COO syringe pressure, the pressure inside of the gas inlet and gas system is also measured with the thermocouple vacuum gauge that is connected to the gas system. This pressure can typically be expected to be less than 8 Torr.

Once the gas is flowing to the interior of the COO syringe, the RF power supply is turned on to its fixed power level. A ENI AWG-6 600 watt RF power supply is used (at 13.56 MHz) at a fixed power level of approximately 30 watts. The RF power supply is connected to a COMDEL CPMX1000 auto match which matched the complex impedance of the plasma (to be created in the COO syringe) to the 50 ohm output impedance of the ENI AWG-6 RF power supply. The forward power is 60 watts and the reflected power is 0 watts so that 30 watts of power is delivered to the interior of the COO syringe. The RF power supply is controlled by a laboratory timer and the power on time set to 5 seconds. Upon initiation of the RF power, a uniform plasma is established inside the interior of the COO syringe. The plasma is maintained for the entire 5 seconds until the RF power is terminated by the timer. The plasma is contemplated to produce a silicon oxide coating of approximately 20 nm thickness on the interior of the COO syringe surface. The coating is expected to function as an oxygen barrier.

After coating, the gas flow is diverted back to the vacuum line and the vacuum valve is closed. The vent valve is then opened, returning the interior of the COO syringe to atmospheric pressure (approximately 760 Torr). The COO syringe is then carefully removed from the vessel holder assembly (after moving the vessel holder assembly out of the electrode assembly).

Example 2

Lubricity Coating

The process of Example 1 is carried out, with the following changes.

The injection molded COO syringe is interior coated with a SiOCH lubricity coating. To accomplish this, the process gas, octamethylcyclotetrasiloxane (OMCTS), is flowed through the gas inlet (under process pressures) into the interior of the COO syringe.

The gas system includes a Horiba VC1310/SEF8240 OMCTS 10SC 4CR heated mass flow vaporization system. The Horiba system is connected to liquid octamethylcyclotetrasiloxane (Alfa Aesar Part Number Al2540, 98%) through a 1/8 in. (approximately 3 mm) diameter PFA tube. The OMCTS flow rate is set to 1.25 sccm. To ensure no condensation of the vaporized OMCTS flow past this point, the gas stream is diverted as described in Example 1.

The pumping system allows the interior of the syringe to be reduced to pressure(s) of less than 100 mTorr. The pressure inside of the COO syringe is approximately 140 mTorr as measured by a capacitance manometer (MKS). The pressure inside of the gas inlet and gas system is typically less than 6 Torr. A fixed power level of approximately 7.5 watts is used. The forward power is 7.5 watts and the reflected power is 0 watts so that 7.5 watts of power is delivered to the interior of the COO syringe. The RF power supply power on time is set to 10 seconds. The plasma is maintained for the entire 10 seconds until the RF power is terminated by the timer. The plasma is contemplated to produce a lubricity coating on the interior of the COO syringe surface.

The invention claimed is:
1. A method of making a syringe comprising:
providing a needle having an outside surface, a delivery outlet at one end, a base at the other end, and an internal passage extending from the base to the delivery outlet;
providing a mold for making a barrel having an interior surface portion defining a lumen and a front passage, the mold comprising a mold core and a mold cavity, the mold core including a leading portion defining the front of the barrel and a needle support projection located at the top of the core where the core contacts the base of the needle, the needle support projection projecting from the leading portion of the core;
positioning at least a portion of the needle within the mold cavity, with its base abutting the needle support projection of the mold core or extending into the mold core and at least a portion of its outside surface exposed within the mold cavity;
injection molding the barrel by injecting moldable material into the mold cavity, forming the portion of the barrel defining the front opening against the portion of the needle outside surface exposed within the mold cavity to join the barrel and the needle with the needle base displaced from the interior surface portion of the syringe barrel; and shrinking the molding material to put the base of the needle at a location that will be flush with the interior surface portion of the syringe barrel.

2. The method of making a syringe of claim 1, in which the barrel comprises a generally hemispheric surface adjacent to the front passage.

3. The method of making a syringe of claim 1, further comprising applying a PECVD barrier layer on at least the hemispheric interior surface portion of the barrel.

4. The method of making a syringe of claim 3, in which the barrier layer forms a barrier between the base of the needle and the generally cylindrical interior surface portion of the barrel.

5. The method of making a syringe of claim 3, in which the barrier layer comprises $SiO_x$, in which x is from about 1.5 to about 2.9.

6. The method of making a syringe of claim 3, in which the barrier layer is effective to provide an oxygen barrier.

7. The method of making a syringe of claim 3, further comprising subsequently prefilling the syringe with a fluid, wherein the barrier layer is effective to reduce leaching of the material of the barrel into the fluid.

8. The method of making a syringe of claim 1, further comprising applying a PECVD-applied lubricity coating on at least a portion of the interior surface portion of the barrel.

9. The method of making a syringe of claim 1, in which the needle outside surface has a non-cylindrical portion within at least a portion of the barrel front passage for anchoring it within the barrel.

10. The method of making a syringe of claim 1, in which the needle is a hypodermic needle.

11. The method of making a syringe of claim 1, in which the barrel is injection molded.

12. The method of making a syringe of claim 1, in which the barrel is made of a cyclic olefin copolymer (COC) layer and a polyethylene terephthalate (PET) layer.

13. The method of making a syringe of claim 1, in which the barrel is made of a cyclic olefin copolymer (COC) outer wall and a polyethylene terephthalate (PET) inner wall.

14. The method of making a syringe of claim 1, in which the interior surface portion of the barrel is cylindrical.

* * * * *